United States Patent
Liu

(10) Patent No.: US 10,732,170 B2
(45) Date of Patent: Aug. 4, 2020

(54) QUALITY OF IMMUNOLOGICAL SYNAPSE PREDICTS EFFECTIVENESS OF CHIMERIC ANTIGEN RECEPTOR (CAR) T CELLS

(71) Applicant: Misum Biotechnology, LLC, Bellaire, TX (US)

(72) Inventor: Dongfang Liu, Bellaire, TX (US)

(73) Assignee: MISSUM BIOTECHNOLOGY, LLC, Millburn, NJ (US)

( * ) Notice: Subject to any disclaimer, the term of this patent is extended or adjusted under 35 U.S.C. 154(b) by 129 days.

(21) Appl. No.: 15/749,445

(22) PCT Filed: Jul. 29, 2016

(86) PCT No.: PCT/US2016/447570
§ 371 (c)(1),
(2) Date: Jan. 31, 2018

(87) PCT Pub. No.: WO2017/023770
PCT Pub. Date: Feb. 9, 2017

(65) Prior Publication Data
US 2018/0231523 A1 Aug. 16, 2018

Related U.S. Application Data

(60) Provisional application No. 62/199,812, filed on Jul. 31, 2015.

(51) Int. Cl.
| | |
|---|---|
| *G01N 33/50* | (2006.01) |
| *A61K 35/17* | (2015.01) |
| *C07K 17/02* | (2006.01) |
| *C07K 19/00* | (2006.01) |
| *G01N 33/544* | (2006.01) |
| *A61K 39/00* | (2006.01) |
| *C07K 16/28* | (2006.01) |
| *A61P 35/00* | (2006.01) |
| *C07K 16/30* | (2006.01) |

(52) U.S. Cl.
CPC ......... *G01N 33/5032* (2013.01); *A61K 35/17* (2013.01); *A61K 39/0011* (2013.01); *A61P 35/00* (2018.01); *C07K 16/2803* (2013.01); *C07K 16/2818* (2013.01); *C07K 16/2878* (2013.01); *C07K 16/30* (2013.01); *C07K 17/02* (2013.01); *C07K 19/00* (2013.01); *G01N 33/502* (2013.01); *G01N 33/505* (2013.01); *G01N 33/544* (2013.01); *A61K 2039/5156* (2013.01); *A61K 2039/5158* (2013.01); *C07K 2317/622* (2013.01); *C07K 2319/03* (2013.01); *C07K 2319/33* (2013.01); *G01N 2333/9645* (2013.01); *G01N 2500/00* (2013.01); *G01N 2500/04* (2013.01); *G01N 2500/10* (2013.01)

(58) Field of Classification Search
CPC ... G01N 33/50; G01N 33/5032; G01N 33/574
See application file for complete search history.

(56) References Cited

FOREIGN PATENT DOCUMENTS

| WO | 9420627 | 9/1994 |
|---|---|---|
| WO | 2013126720 A2 | 8/2013 |

OTHER PUBLICATIONS

Philpott et al. (Blood Mar. 15, 1996 87(6): 224-2251), (Year: 1996).*
International Search Report and Written Opinion dated Oct. 20, 2016, in International Application PCT/US16/44757.
Groves, J.T., et al.; Supported Planar Bilayers in Studies on immune Cell Adhesion and Communication; Journal of Immunological Methods; 2003; pp. 19-32, especially abstract pp. 22-24 and 28-29, Fig. 1.
Finney, H.M., et al.; Activation of Resting Human Primary T Cells with Chimeric Receptors: Costirnulation from CD28, Inducible Costimulator, CD134, and CD137 in Series with Signals from the TCR Chain; The Journal of Immunology; 2004; pp. 104-113, especially abstract pp. 109-111.
Gossen et al.; Proc. Natl. Acad. Sci USA 89; 1992; pp. 5547-5551.
Gossen et al.; Trends Biotech; 12; 1994; pp, 58-62.
Crook; EMBO J.; 8; 1989; pp. 513-519.
Sambrook et al. (1989) and Ausubel, Current Protocols in Molecular Biology, Green Publishing Associates and Wiley Interscience, N.Y. (1989), (1994).
Raum et al. Cancer Immunol Immunother (2001) 50(3), 141-150) or pSPORT1 (GIBCO BRL).
Reiss, Plant Physiol. (Life-Sci. Adv,) 13 (1994), 143-149).
Herrera-Estrella, EMBO J. 2 (1983), 987-995).
Scikantha, J. Bact 178 (1996), 121.
Marsh, Gene 32 (1984), 481-485.
Hartman, Proc. Natl. Acad. Sci. USA 85 (1988), 8047.
International Preliminary Report on Patentability dated Jul. 14, 2017, in International Application PCT/US16/44757.
Tamura, Biosci. Biotechnol. Biochem. 59 (1995), 2336-2338.
Giacornin, PI. Sci. 116 (1996), 59-72; Scikantha, J. Bact. 178 (1996), 121.
Gerdes, FEBS Lett. 389 (1996), 44-47.
Jefferson, EMBO J. 6 (1987); 3901-3907.
Straathof et al., Blood 105:4247-4254 (2005).
Xiong, Wei, et al.; Immunological Synapse Predicts Effectiveness of Chimeric Antigen Receptor Cells; Molecular Therapy; Apr. 2018; vol. 26; No. 4.
Dustin, M.L., et al., The Immunological Synapse, Cancer Immunology Research, vol. 2, No. 11, 1 Nov. 2014, pp. 1023-1033.
Dustin, M.L., Hunters to Gatherer and Back: Immunological Synapses and Kinapses as Variations of the Theme of Amoeboid Locomotion, Annual Review of Cell and Developmental Biology, vol. 24, No. 1, Nov. 1, 2008, pp. 577-596.

(Continued)

*Primary Examiner* — Peter J Reddig
(74) *Attorney, Agent, or Firm* — Wilson Sonsini Goodrich & Rosati, P.C.

(57) ABSTRACT

Embodiments of the disclosure concern methods of determining the effectiveness of immune cells, such as T cells, with particular chimeric antigen receptors. In specific embodiments, a synapse between the CAR and the tumor antigen is measured for structure, signaling, and functionality by imaging. As such, the quality of the synapse is determined and positively correlates with effectiveness of the particular CAR immune cells.

18 Claims, 21 Drawing Sheets
(17 of 21 Drawing Sheet(s) Filed in Color)

(56) References Cited

OTHER PUBLICATIONS

European Search Report (ESR) dated Mar. 25, 2019 for EP Appl. No. 16833620.4.
Kowolik et al. CD28 costimulation provided through a CD19-specific chimeric antigen receptor enhances in vivo persistence and antitumor efficacy of adoptively transferred T cells. Cancer Res 66(22):10995-11004 (2006).
Liu, Dongfang, et al., Structured Illumination Microscopy Improves Visualization of Lytic Granules in HIV-1 Specific Cytotoxic T-Lymphocyte Immunological Synapses, AIDS Research and Human Retroviruses, vol. 31, No. 9, Apr. 1, 2015, pp. 866-867.
Mescher, M.F., et al., Stimulation of Tumor-Specific Immunity Using Tumor Cell Plasma Membrane Antigen, MET Academic Press, US, vol. 12, No. 2, Jun. 1, 1997.
Rappl, Gunter et al., The CD3-Zeta Chimeric Antigen Receptor Overcomes TCR Hypo-Responsiveness of Human Terminal Late-Stage T Cells, PLOS ONE, vol. 7, No. 1, Jan. 23, 2012.
Song et al. In Vivo Persistence, Tumor Localization, and Antitumor Activity of Car-Engineered T Cells Is Enhanced by Costimulatory Signaling through CD137 (4-1BB). Cancer Res 71(13):4617-4627 (2011).
Vardhana, Santosha et al., Supported Planar Bilayers for the Formation of Study of Immunological Synapses and Kinapse, Journal of Visualized Experiments, No. 19, Sep. 15, 2008.
Zheng, Peilin et al., Super-resolution Imaging of the Natural Killer Cell Immunological Synapse on a Glass-supported Planar Lipid Bilayer, Journal of Visualized Experiments, vol. 3791, No. 96, Jan. 1, 2015.

* cited by examiner

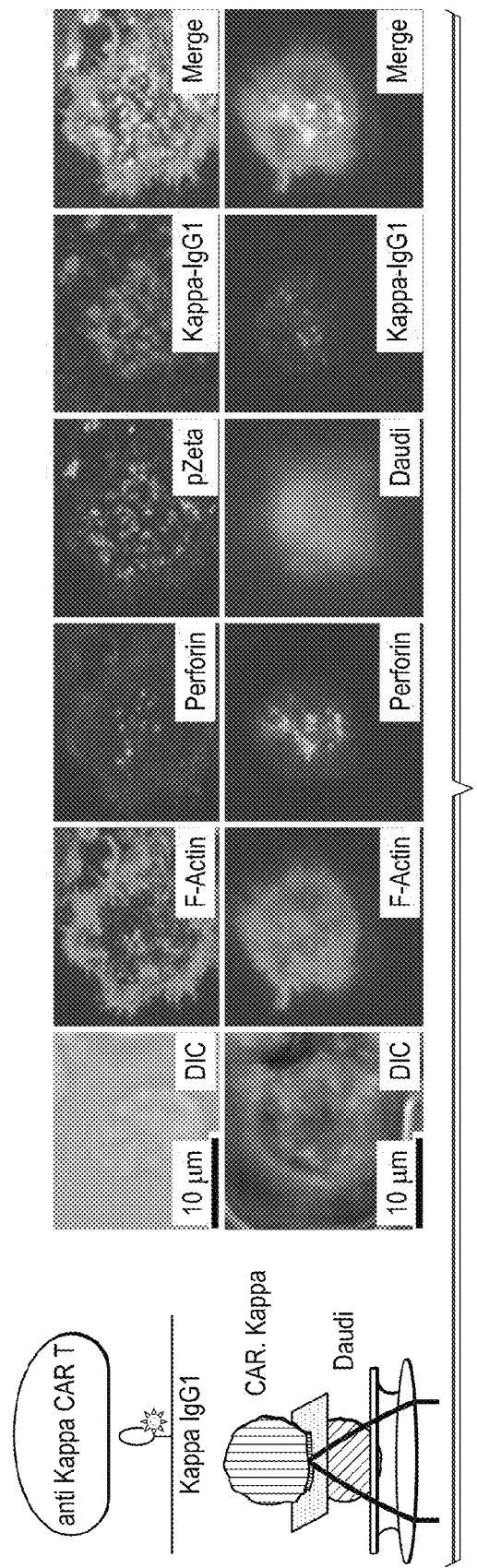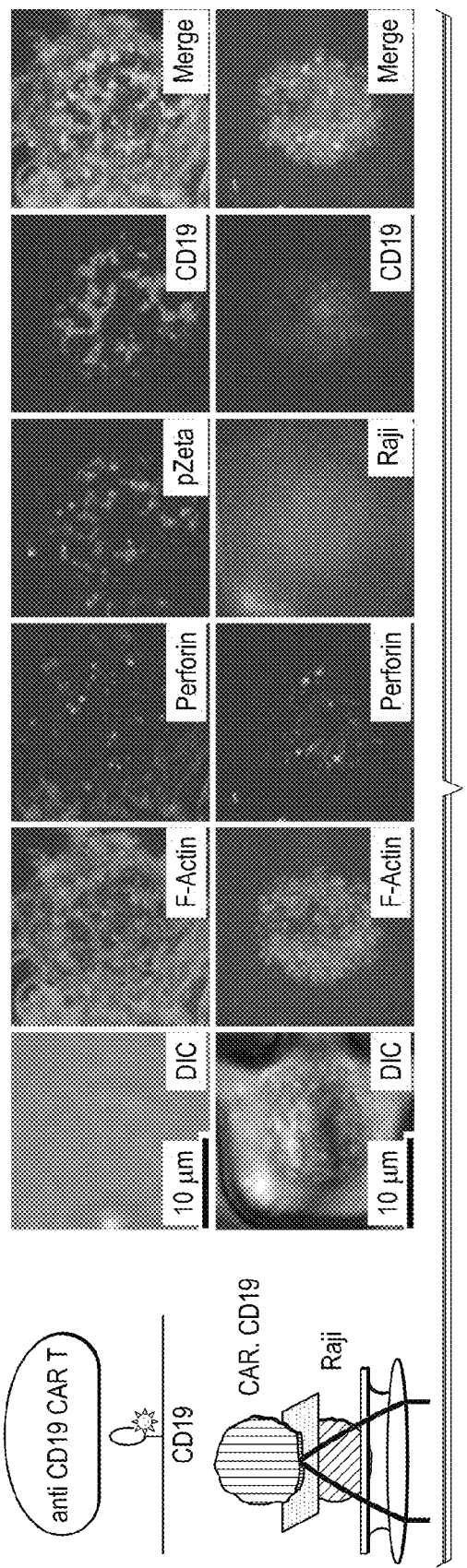
FIG. 1A
FIG. 1B

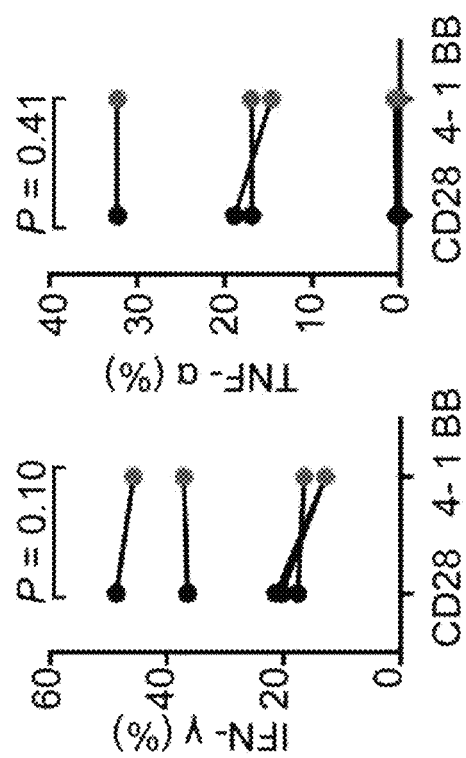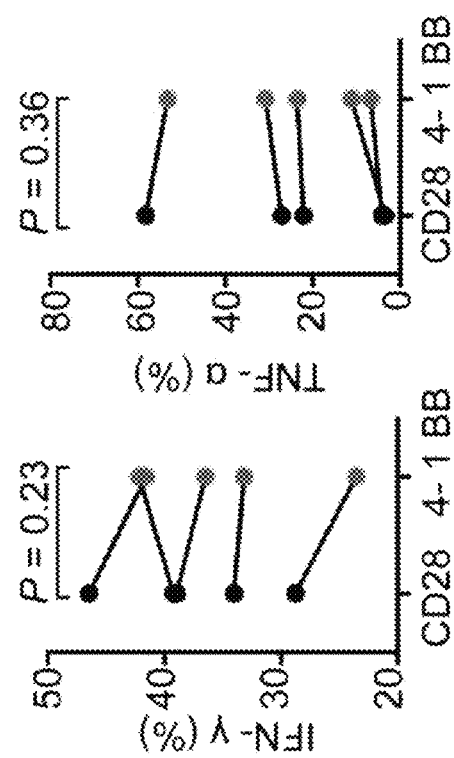

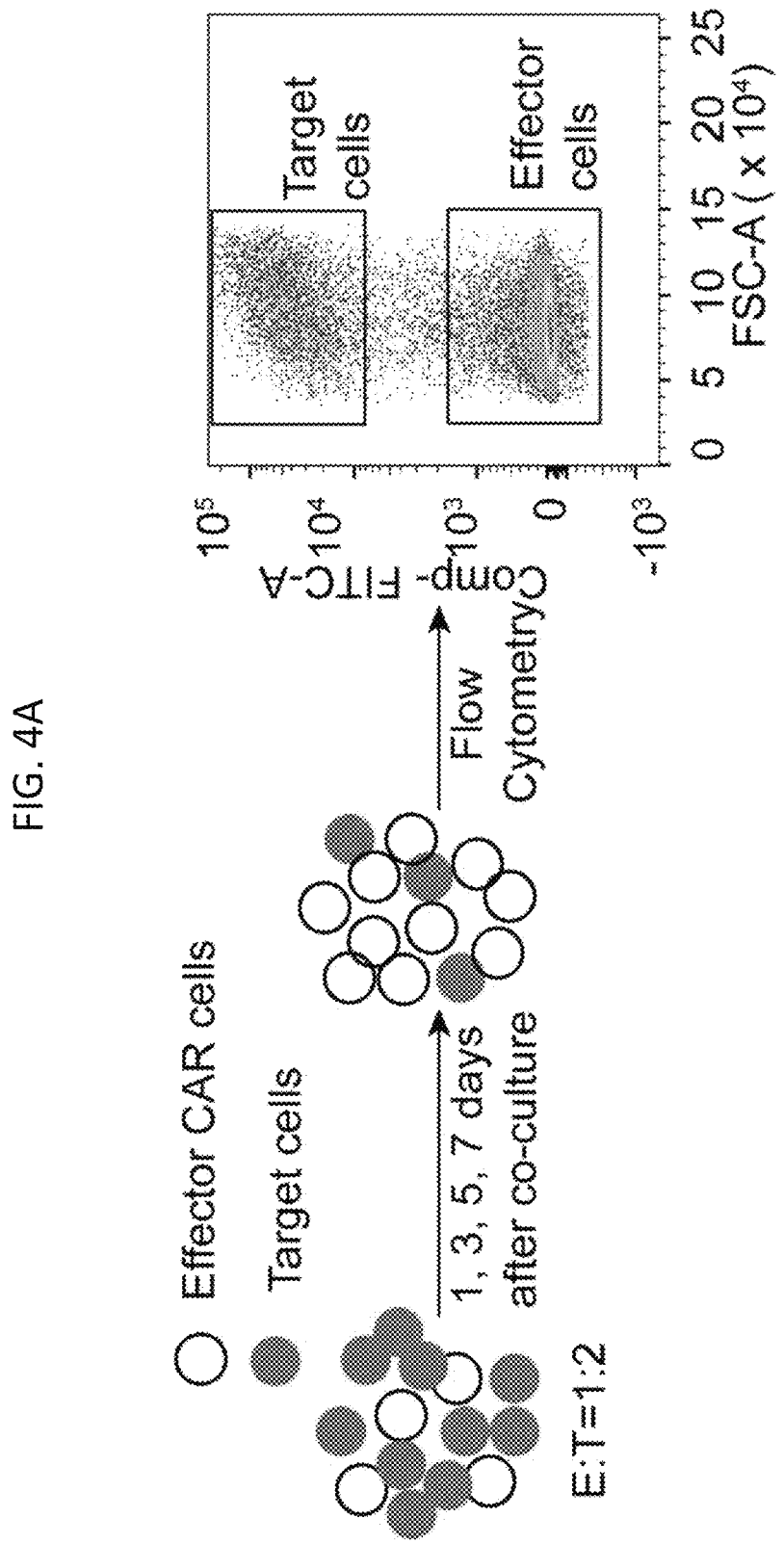

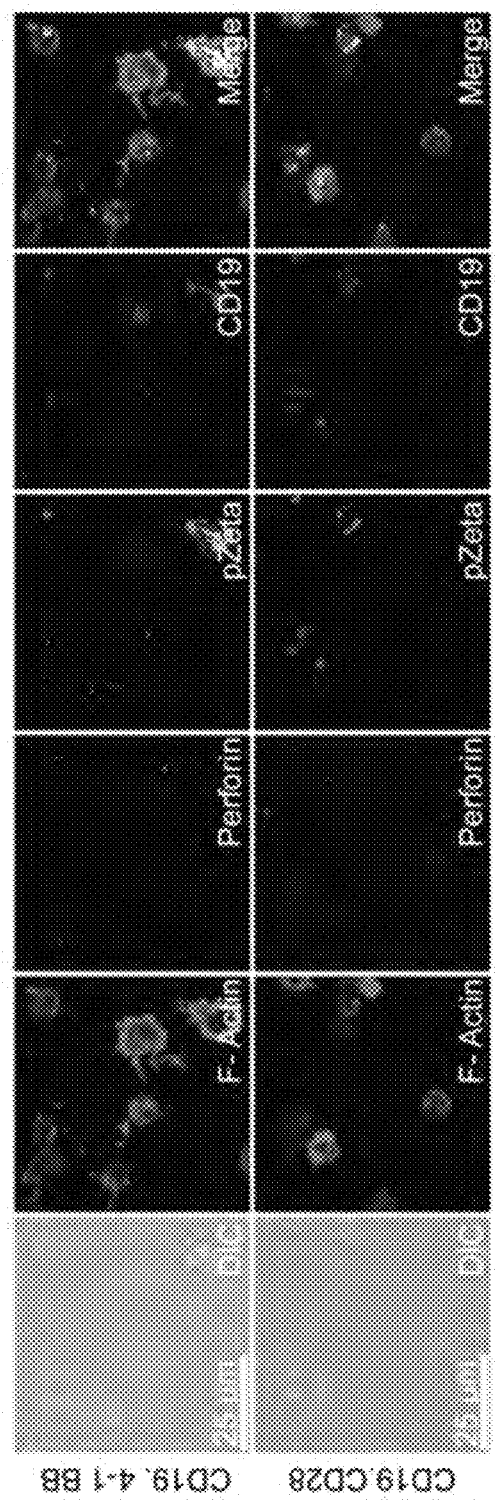

QUALITY OF IMMUNOLOGICAL SYNAPSE PREDICTS EFFECTIVENESS OF CHIMERIC ANTIGEN RECEPTOR (CAR) T CELLS

This application is the National Stage of International Application No. PCT/US16/44757, filed on Jul. 29, 2016; which claims the benefit of U.S. Provisional Application No. 62/199,812, filed on Jul. 31, 2015; both of which are incorporated herein in their entirety.

STATEMENT REGARDING FEDERALLY SPONSORED RESEARCH OR DEVELOPMENT

This invention was made with government support under grant P30 A1036211 awarded by the National Institutes of Health and grant 5P50CA126752-09 awarded by the National Cancer Institute. The government has certain rights in the invention.

TECHNICAL FIELD

Embodiments of the disclosure concern at least the fields of cell biology, molecular biology, immunology, and medicine.

BACKGROUND

Recent progress using adoptive T cell-based therapy with chimeric antigen receptors (CAR) shows impressive successes in patients with cancer by enhancing the effectiveness of CAR T cells. A major gap in the current knowledge is having an easy way to predict the effectiveness of CAR T cells. Specifically, many scientists from different laboratories are generating different CARs with minor modifications. However, before these modified CARs can enter clinical trials, it is essential that they be evaluated accurately for their quality, safety and potential effectiveness, in a cost-effective manner. The conventional tools for immunological analyses of quality and effectiveness are time-consuming, labor intensive, costly, and inaccurate.

The immunological synapse (IS) was originally described by imaging T-cell interactions with antigen-presenting cells (APCs). The structure, function, and signaling cascades at the synapses have been further confirmed by imaging of T-cell interactions with the glass-supported planar lipid bilayer containing the MHC-peptide complex and other co-stimulatory molecules. The general consensus in the field of immunology is that the glass-supported planar lipid bilayer system can be used for mimicking the target cells to study synapses at high resolution. Although tremendous progress has been made in the basic research on the IS, with a focus on the structure, function, and signaling cascades, to date no study has addressed how the synapse of the CAR controls CAR T cell activation.

The present disclosure provides a solution to a long-felt need in the art how to measure the efficacy of therapeutic immune cells, including CAR T cells.

BRIEF SUMMARY

The present invention is directed to a system and methods for determining the efficacy of cells that bear one or more antigen-recognizing moieties. In specific embodiments, the moieties comprise Chimeric Antigen Receptors (CARs), engineered T-cell receptors (TCR) and other natural activating receptors, such as natural-killer group 2, member D (NKG2D)-based immunotherapy.

In certain embodiments, the methods and compositions of the disclosure provide determination of the efficacy of particular therapeutic cells, including therapeutic immune cells, such as non-natural therapeutic immune cells. In specific embodiments, the immune cells are capable of binding to a particular antigen, including a tumor antigen. The immune cells may express one or more CARs.

In particular embodiments, the effectiveness of CAR-bearing immune cells, including at least T cells or NK cells, and other cytotoxic lymphocytes (e.g. NKT cells), is predicted by and/or determined by the quality of an immunological synapse between the CAR and its target antigen using structural and functional parameters, in addition to downstream signaling cascades following interaction at the synapse, in certain embodiments. In particular embodiments, methods employing imaging are utilized to measure the immunological synapse and/or how the synapse of the CAR itself controls CAR T cell activation.

In at least some embodiments, an immunological synapse refers to interaction of an immune cell with any other type of cell (including other type of immune cells), such as a T cell and an antigen presenting cell (APC), such as interaction of T cell antigen receptors with major histocompatibility complex molecule-peptide complexes.

In embodiments of the disclosure, an immunological synapse predicts effectiveness of Chimeric Antigen Receptor (CAR) T cells, and in at least some cases visualization of the synapse is achieved by one or both of two complementary systems. Each system may be in vitro or in vivo system, and each system may utilize whole cell analysis or analysis using other than whole cells, such as membranes that mimic a cell membrane.

Embodiments of the disclosure include methods that can ascertain whether or not a particular CAR T cell can form a stable immunological synapse.

Certain embodiments concern the quantitation and/or determination of quality of the structure, signaling, and/or function of one or more CAR-comprising cells, such as CAR T cells. In specific embodiments, the integrity of the immunological synapse of more than one type of CAR on one or more CAR T cells is ascertained. In specific embodiments one can assay the proficiency of more than one CAR at a time. In certain embodiments, more than one type of CAR on a single cell is assayed and/or assaying of multiple cells with different CARs simultaneously. In such cases, non-identical labels may be employed within the same system to distinguish different CARs and/or their respective antigens.

Any component of the system may be labeled, including by standard means in the art, such as the CAR itself, an antigen to which the CAR binds, a T cell component, a B cell component, a ligand for the costimulatory receptor or any cytokine produced by immune cells (including T, B, DC, and NK cells), and so forth.

Embodiments of the disclosure concern a system comprising a lipid bilayer that has structural and functional attributes that allow its use as a mimic of an immunological synapse.

Embodiments of the disclosure include a glass-supported planar lipid bilayer (SLB) system. One of the most useful applications of this technique has been in the study of immunological synapse formation due to the ability of the SLBs to mimic the surface of a target cell while forming a horizontal interface. This approach disposed of antigen presenting cells (APCs) or any immune cells in favor of a glass-supported planar lipid surface, into which proteins could be attached and move freely in two dimensions. Using this method, individuals were able to see directly up into the synapse using high resolution fluorescence microscopy, and for the first time get a "face-to-face" look at the structure of the immunological synapse.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee. For a more complete understanding of the present invention, reference is now made to the following descriptions taken in conjunction with the accompanying drawing, in which:

FIG. 1: Visualization of CAR T cell immunological synapse (a) Diagram of lipid bilayer containing Alexa Fluor 647-labeled human kappa IgG1 (left) and confocal images of the CAR synapse on the lipid bilayer carrying Alexa Fluor 647-labeled human kappa IgG1 (right). In the lower panel, a schematic model of VCP system (left) and confocal images of a kappa-CAR T cell conjugated with a kappa chain positive pre-stained Daudi cell (cyan) (right). (b) Diagram of lipid bilayer containing Alexa Fluor 568-labeled CD19 (left) and confocal images of a representative kappa-CAR T cell on the lipid bilayer carrying Alexa Fluor 568-CD19 (right). In the lower panel, a schematic model of the VCP system with CD19-CAR T and its susceptible Raji cell (left) and confocal images of CD19-CAR T cells conjugated with CD19 positive Raji cells (cyan) using VCP system (right). Fixed and permeabilized CAR T cells were stained for Ab against perforin (green), pZeta (cyan), and F-actin (magenta), respectively. Scale bars represent 10.0 μm. DIC=Differential interference contrast

(a) CAR. Kappa T cells were isolated from four different healthy donors and transduced with 4-1BB and CD28 constructs. The target Daudi cells expressing fluorescent protein mCherry were mixed with CAR T cells for 7 days. The number of both target cells and CAR T cells were counted by flow cytometry. (b) CAR.CD19 T cells were isolated from four different healthy donors and transduced with 4-1 BB and CD28 constructs. The Raji-GFP target cells were mixed with CAR T cells for 7 days. The number of both target cells and CAR T cells were measured by flow cytometry.

Figure 11:
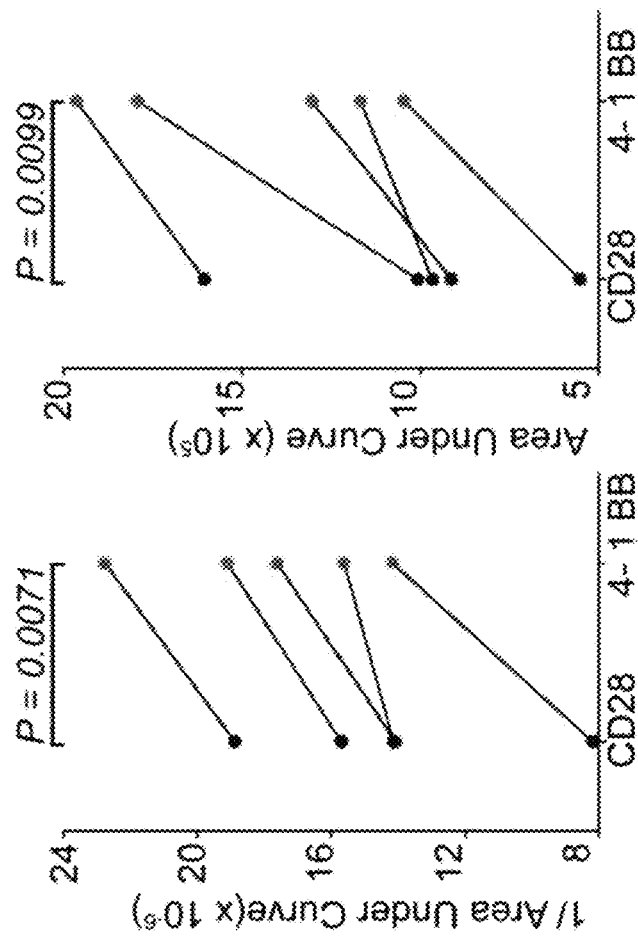

FIG. 11: Superior anti-tumor activity from 4-1BB-kappa-CAR T cells from five individuals. PBMCs from five healthy donors were transduced with 4-1BB kappa-CAR (red dots) or CD28 kappa-CAR (black dots) retrovirus. The reciprocal of the area under the curve of target cell numbers (killing efficiency, left) and area under the curve of effector cell numbers from kappa-CAR T cells (proliferation efficiency, right) were calculated, respectively. The transduced CAR T cells were activated by co-culturing with a kappa-positive Daudi cell line to quantify the anti-tumor activity. Data pooled from two independent experiments. P value is for paired t-test.

Figure 12:
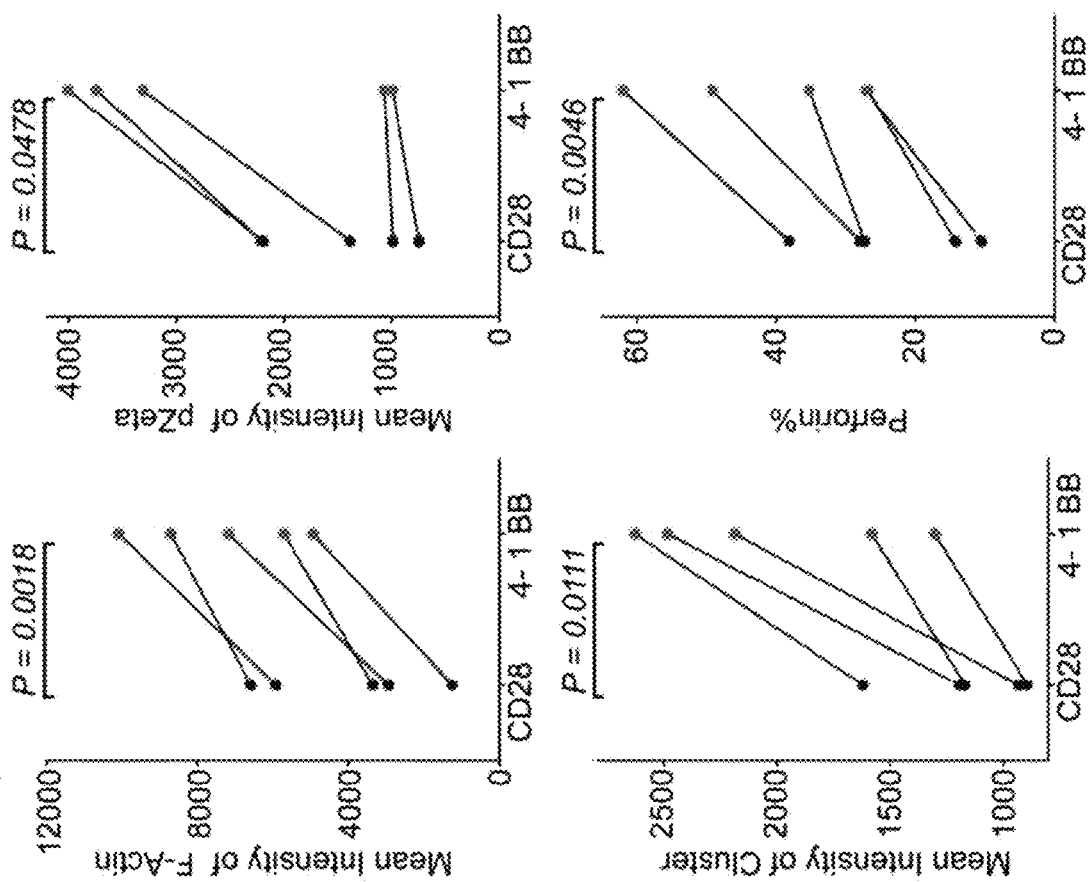

FIG. 12: 4-1BB-CAR T cells show higher IS quality from five individuals. PBMCs from five healthy donors were transduced with kappa-4-1BB-CAR (red dots) or kappa-CD28-CAR construct (black dots) retrovirus. The MFI of F-actin, pZeta, antigen cluster, and percentage of perforin polarization from kappa-CAR T cells were calculated. The transduced CAR T cells were activated by bilayers carrying kappa-Alexa Fluor 647 to quantify the MFI on the plasma membrane to evaluate the IS quality. Data pooled from two independent experiments. P value is for paired t-test.

DETAILED DESCRIPTION

I. Definitions

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein embodiments which are disclosed and still obtain a like or similar result without departing from the spirit and scope of the invention.

The term "immunological synapse" as used herein refers to an interface between an an immune cell with any other type of cell (including another immune cell, including another type of immune cell, such as an antigen-presenting cell or target cell and a lymphocyte, such as an effector T cell).

II. General Embodiments

Embodiments of the disclosure concern methods and compositions that employ systems to ascertain the use of one or more populations of cells in need for determining their therapeutic efficacy. The system may utilize one assay or two or more assays to test cells from the same population, and the assays may be in vitro or in vivo. In certain embodiments, a lipid bilayer system is utilized to determine efficacy of binding to an antigen within the membrane and subsequent downstream events to the binding.

Herein, a glass-supported planar lipid bilayer system was applied to study a CAR synapse with its target antigen at high resolution. The analysis included visual aspects, and the images revealed several properties of a CAR synapse including antigen binding that directly mirrored the distribution of CAR proteins on CAR T cells and that are accumulated at the center of the synapse. Multiple parameters predicted the effectiveness of the CAR T cell, and in specific embodiments the effectiveness is measured by one or both of tumor cell numbers and T-cell proliferation during long-term killing assay. In additional embodiments, a novel imaging system was developed to study the CAR T cell's immunological synapse horizontally in a high-throughput manner. The vertical cell pairing (VCP) system enables imaging of the CAR T cell's immunological synapse in a horizontal focal plane on both fixed- and live-cell imaging. In specific embodiments, the quality of the immunological synapse can predict the effectiveness of CAR T cells, which provides the field of immunotherapy a novel strategy to advance the development of CAR T therapies.

III. Determining Efficacy of Gene-Modified Immune Cells

Embodiments of the disclosure concern determining the efficacy of any modified immune cell, such as a gene-modified immune cell. The immune cell may be of any kind, including a T cell, NK cell, NKT cells, or dendritic cell. The cells may be modified by any means, including by expression of an exogenously added vector, for example. The cells may be modified to express a chimeric antigen receptor (CAR), an engineered T-cell receptor, and so forth.

Adoptive cell-based therapy using CAR-modified immune cells is useful to improve the overall survival of patients with malignancies by enhancing the effectiveness of T cells. Precisely predicting the effectiveness of a variety of CAR T cells represents one of today's key unsolved problems in immunotherapy. Optimal function of T cells depends on the quality of the immunological synapse. However, key differences in the synapse formed by effective versus less-effective CART cells with their susceptible tumor cells remain unclear. In the present disclosure, the effectiveness of CAR T cells is predicted at least by evaluating the quality of the CAR T synapse through a variety of parameters, such as by quantitation of F-actin, central clustering of tumor antigen, polarization of lytic granule, and/or distribution of key signaling molecules within synapses. As shown in the specific examples herein, long-term killing capability correlates positively with the quality of the synapse in two different CAR T cells that share identical antigen specificity. In certain embodiments, the quality of the synapse correlates with performance of CAR T cells in vitro. Therefore, in specific embodiments the quality of the synapse predicts the effectiveness of CAR T cells, which provides a novel strategy to direct CAR T therapy.

In certain embodiments, an in vitro system is utilized to ascertain the efficacy of one or more CAR T cells. The in vitro system may employ the use of one or more lipid bilayers to mimic a cell membrane, and in such cases the lipid bilayer may comprise one or more moieties to which a particular CAR T cell may be able to bind. In specific embodiments, one or more moieties in the lipid bilayer is labeled, and the labeling may be of any kind, including fluorescent, radioactive, or colorimetric, for example. In particular embodiments, the lipid bilayer is affixed to a substrate, and in specific embodiments, the substrate is glass, plastic, any type of material that can support the lipid bilayer (PDMS, polydimethylsiloxane), and so forth.

In particular embodiments, a system is employed that utilizes cellular analysis between two or more cell types and such a system may or may not be a high throughput system. The system in high throughput form may be able to analyze at least 1, 10, 100, 1000, 1500, or 2000, 3000, or more conjugates at a time with high loading efficiency. In specific embodiments, the system is a vertical cell pairing (VCP) system (see FIG. 1) that allows analysis of the immunological synapse of the CAR T cells with one or more other types of cells using imaging. In particular embodiments, the cell type employs CAR T cells and antigen presenting cells, such as B cells. In certain embodiments the VCP system enables imaging in a horizontal focal plane, and one or both types of cells may be fixed for imaging. In specific embodiments, the cells are live upon imaging. Using a VCP system, a 'face-to-face' look at the structure and signaling of the IS of the CAR T cells is provided for the first time.

In particular embodiments, the efficacy of an immunological synapse is determined in a variety of means, including structural and functional, in addition to the ability to effectively elicit appropriate signaling cascade(s). Particular distributions of CARs bound to corresponding tumor antigens located within a lipid bilayer, for example, is structurally indicative of an efficacious CAR. For example, one can evaluate the quality of the CAR T synapse, including by quantitation of F-actin (Intensity), central clustering of tumor antigen (distribution and intensity), polarization of lytic granule (distribution and localization), and/or distribution/fluorescence intensity of key signaling molecules within synapses.

In certain embodiments, the quality of an immunological synapse is ascertained by determining the ability to sufficiently activate intracellular downstream signaling. A variety of downstream signaling members may be investigated, including more than one, either at the same time or at different times. In specific embodiments the determination utilize antibodies (one could also use fluorescently-labeled signaling molecules or other technique-labeled signaling molecules, such as enzyme or radio-material) to the one or more members of downstream signaling. In particular embodiments, one may assay for one or more of the following: 1) phosphorylation of the zeta chain on the CAR, which is indicative of effective CAR signaling, and pZeta is a proximal CAR signaling molecule; 2) F-actin, which is revealing of synapse stability; 3) perforin, which is indicative of lytic granules; 4) pZAP70, part of a distal signaling pathway and indicative of long-term proliferation and differentiation of activated T lymphocytes; 5) Lck, part of a distal signaling pathway and indicative of long-term proliferation and differentiation of activated T lymphocytes; 6) measurement of killing activity against tumor cells, such as by measurement of the cytotoxicity of CAR T cells; 7) intracellular cytokine secretion (such as production of TNF-α and/or IFN-γ and/or IL-2 and/or other cytokines; 8) proliferation capability; 9) killing efficiency, such as killing of desired cells, including cancer cells and/or T-regulatory cells For example, although the phosphorylation of zeta chain on the CAR may be analyzed by any means, in specific embodiments one may analyze the phosphorylation with antibodies against a phosphorylation site, such as at tyrosine 83. When the co-localization of the particular antibody is synchronous with the particular tumor antigen on lipid bilayers, one can ascertain the distribution of the CAR on T cells. One can ascertain specific CAR signaling. In some embodiments, one can compare the CAR signaling with endogenous TCR signaling or other costimulatory receptor signaling. In embodiments that regard F-actin as a direct or indirect indicator of CAR T cell efficacy, a strong accumulation of F-actin at the immunological synapse indicates that the CAR is functional. Based on statistical analysis, in specific embodiments F-actin is a useful predictor for immunological synapse quality. That is, in specific embodiments, the stronger the F-actin staining is at the immunological synapse, the better the CAR T cell function. In particular embodiments, using F-actin as a single predicator is useful, such as for in vivo synapse study. In specific embodiments, the fluorescence intensity of F-actin at an immunological synapse is relative to another region in the cells. In certain embodiments, polarization of perforin is an indicator of a functional CAR.

In particular embodiments, the functionality of a particular CAR being tested is in a system that mimics the complex surface of a tumor cell to a higher degree than a lipid bilayer. In such embodiments, whole cells may be utilized in the system to ascertain the structural and functional effectiveness of a certain CAR on an actual cell. Such a system may or may not be a high throughput system, and in specific embodiments the system is a vertical cell pairing system that investigates the interaction of two or more cells by imaging. In such a system, a plurality of CAR T cells and a plurality of APC cells, such as B cells, may be employed to assay for an accumulation of a tumor antigen at an immunological synapse. In one embodiment, the CAR T cells are fixed, and in another embodiment the APC cells are fixed.

The efficacy of the cells may be measured in a variety of ways. In specific embodiments, one compares a variety of CARs sharing identical antigen specificity. By ranking the quality of synapse, one can determine the most effective CAR for clinical use. In specific embodiments, both qualitative and quantitative measures are applied to determine efficacy. In particular embodiments, the present disclosure provides an easy-to-use approach to assess the effectiveness of CAR T cell and represents an important, unsolved problem in the field of immunotherapy. In certain embodiments, one can rank the predicted effectiveness of a variety of CARs with minor modifications that cannot otherwise be distinguished by conventional immunological analyses, such as cytokine secretion, proliferation assay, and cytotoxicity assay. The current strategies to determine efficacy of CAR T-cells utilizes a conventional in vitro method that concerns cytokine secretion, cytotoxicity, proliferation, and/or long-term killing assay or utilizes an in vivo mouse mode. These currently available strategies including conventional immunologic analysis in vitro and in vivo are time-consuming, labor intensive, costly, and inaccurate, in contrast to the methods of the disclosure.

Although any type of CAR may be investigated with methods of the disclosure, including having none or one or more co-stimulatory domains in the CAR, in specific embodiment the CAR comprises at least 4-1BB.

In particular embodiments, methods of the disclosure include three-dimensional microscopy, including microscopy methods that are known in the art, such as conventional confocal microscopy.

IV. Lipid Bilayers

Embodiments of the disclosure include lipid bilayers for quality testing of one or more types of therapeutic cells, such as immune cells that express one or more particular moieties that have at least the potential activity of rendering the immune cells therapeutic. In particular embodiments, the immune cells are non-natural and comprise a receptor that expresses a moiety that binds an antigen. The moiety may be an antibody of any kind, for example.

In particular embodiments, a lipid bilayer system is utilized as a composition for testing whether or not a particular type of cells are effective for an intended purpose. The system may have an output that informs a direct or indirect user whether or not the particular cells in question will be effective for an intended purpose. The output may be quantitative, qualitative, or both. The output may be visual, colorimetric, radioactive, digital, electronic, and so forth.

In certain embodiments, the lipid bilayer comprises one or more antigens that are labeled, and the label may be of any kind, including fluorescent, radioactive, colored, and so forth. A plurality of cells being tested for one or more attributes is provided to the lipid bilayer and allowed for binding. Where appropriate, the binding is of a moiety at least part of which is on the outside of the cell to the antigen(s). Upon binding of the moiety to the antigen, a complex is formed between the antigen and the cells. The complex may be analyzed in one or more ways, including structurally and/or functionally, for example. The distribution of complexes within the lipid bilayer may or may not be determined.

Binding of the cell to the antigen may be assayed in one or more ways. The binding may be assayed by measuring downstream signaling, key signaling molecules in the synapse, or both, for example.

The lipid bilayer may be generated by standard means in the art, such as fusing liposome droplets with glass substrates. The system including the lipid bilayer may be monitored. The system may be visualized, such as by microscopy, including by confocal microscopy, epifluorescence microscopy, and so forth. With the recent advent of a variety of super-resolution techniques, such as SIM (structured illumination microscopy), PALM (photoactivated localization microscopy), STORM (stochastical optical reconstruction microscopy), and STED (stimulated emission depletion), investigators are now able to study these synaptic structures in unprecedented detail, which has in turn provided an increasingly clarified understanding of the IS. Thus, in specific embodiments, super-resolution STED/SIM/PLAM and live cell total internal reflection fluorescence (TIRF) microscopes (TIRFM) are employed.

In specific embodiments, the lipid bilayer is comprised of chloroform-suspended stock solutions of 1,2-dioleoyl-sn-glycero-3-phosphocholine (DOPC) and 1,2-dioleoyl-sn-glycero-3-phosphoethanolamine-N-cap biotinyl (Biotin-PE) to make diluted stocks at the desired final concentration.

V. Examples of Chimeric Antigen Receptors for Testing

Genetic engineering of immune cells (such as human T lymphocytes) to express tumor-directed chimeric antigen receptors (CAR) can produce antitumor effector cells. In certain embodiments of the invention there are immune cells that are modified to comprise at least a CAR. Any of the methods encompassed herein for testing effectiveness of a CAR may involve the testing of any cell that comprises a CAR for any antigen of any kind. In specific embodiments, the antigen is a tumor antigen.

In particular cases, the cells are cytotoxic T lymphocytes (CTLs) that include a receptor that is chimeric, non-natural and engineered at least in part by the hand of man. In particular cases, the engineered CAR has one, two, three, four, or more components, and in some embodiments the one or more components facilitate targeting or binding of the T lymphocyte to a tumor antigen-comprising cancer cell. In specific embodiments, the CAR comprises an antibody for a tumor antigen, part or all of a cytoplasmic signaling domain, and/or part or all of one or more co-stimulatory molecules, for example endodomains of co-stimulatory molecules. In alternative embodiments, no endodomains of co-stimulatory molecules are utilized. In specific embodiments, the antibody is a single-chain variable fragment (scFv).

In certain embodiments, a cytoplasmic signaling domain, such as those derived from the T cell receptor ζ-chain, is employed as at least part of the chimeric receptor in order to produce stimulatory signals for T lymphocyte proliferation and effector function following engagement of the chimeric receptor with the target antigen. Examples would include, but are not limited to, endodomains from co-stimulatory molecules such as CD28, CD27, 4-1BB (CD137), OX40 (CD134), ICOS, Myd88, and/or CD40. In particular embodiments, co-stimulatory molecules are employed to enhance the activation, proliferation, and cytotoxicity of T cells produced by the CAR after antigen engagement. T-cells can also be further genetically modified to enhance their function. Examples, but not limited to, include the transgenic expression of cytokines (e.g. IL2, IL7, IL15), silencing of negative regulators (for example SHP-1, FAS, PD-L1), chemokine receptors (e.g. CXCR2, CCR2b), dominant negative receptors (e.g. dominant negative TGFβRII), and/or so called 'signal converters' that convert a negative into a positive signal (e.g. IL4/IL2 chimeric cytokine receptor, IL4/IL7 chimeric cytokine receptor, or TGFβRII/TLR chimeric receptor).

In a particular embodiment, the components of the CAR in the polynucleotide that encodes it are in a particular order so that the expressed CAR protein has the corresponding domains in a particular order. For example, in particular embodiments the transmembrane domain is configured between the antibody domain and the endodomain. In specific embodiments, the order of the domains in the encoded CAR protein is N-terminal-antibody-transmembrane domain-endodomain-C terminal, although in certain cases the order of the domains in the encoded CAR protein is N-terminal-endodomain-transmembrane domain-antibody-C terminal. Of course, other domains may be inserted within this configuration, with care being taken to place it on the appropriate side of the transmembrane domain to be located inside the cell or on the surface of the cell. Those domains that need to be intracellular need to be on the flank of the transmembrane domain in the protein that the endodomain is located, for example. Those domains that need to be extracellular need to be on the flank of the transmembrane domain in the protein that the antibody is located.

The CAR may be first generation (CAR that includes the intracellular domain from the CD3 ξ-chain), second generation (CAR that also includes intracellular signaling domains from various costimulatory protein receptors (e.g., CD28, 41BB, ICOS)), or third generation (CAR in which there are multiple signaling domains, such as when signaling is provided by CD3-ζ together with co-stimulation provided by CD28 and a member of the tumor necrosis factor receptor superfamily, such as 4-1BB or OX40), for example. In specific embodiments the CAR comprises a single costimulatory domain, however.

The CAR may be specific a TAA or TSA, e.g., such as those specific for EphA2, HER2, GD2, Glypican-3, 5T4, 8H9, $\alpha_v\beta_6$ integrin, B cell maturation antigen (BCMA) B7-H3, B7-H6, CAIX, CA9, CD19, CD20, CD22, kappa light chain, CD30, CD33, CD38, CD44, CD44v6, CD44v7/ 8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor α, GD2, GD3, HLA-AI MAGE A1, HLA-A2, IL11Ra, IL13Ra2, KDR, Lambda, Lewis-Y, MCSP, Mesothelin, Muc1, Muc16, NCAM, NKG2D ligands, NY-ESO-1, PRAME, PSCA, PSC1, PSMA, ROR1, Sp17, SURVIVIN, TAG72, TEM1, TEM8, VEGRR2, carcinoembryonic antigen, HMW-MAA, VEGF receptors, Galectin, and/or other exemplary antigens that are present with in the extracelluar matrix of tumors, such as oncofetal variants of fibronectin, tenascin, or necrotic regions of tumors and other tumor-associated antigens or actionable mutations that are identified through genomic analysis and or differential expression studies of tumors, for example.

In certain embodiments, a CAR that directs an immune cell to one or more tumor antigen comprises (1) an extracellular antigen-binding domain that binds to one or more tumor antigen, and (2) an intracellular domain that comprises a primary signaling moiety, e.g., a CD3ζ chain, that provides a primary T cell activation signal, and optionally a costimulatory moiety, e.g., a CD28 polypeptide and/or a 4-1BB (CD137) polypeptide.

Although in some embodiments the scFv is of any kind, in other embodiments the scFv is derived from specific monoclonal antibodies.

III. Host Cells Expressing the CARs

Methods of the disclosure concern measurements of the effectiveness of any kind of CAR, wherein the CAR may reside in any type of cell, including an immune cell, such as a therapeutic immune cell. As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a cytotoxic T-cell (also known as TC, Cytotoxic T Lymphocyte, CTL, T-Killer cell, cytolytic T cell, CD8+ T-cells, CD4+ T-cells, or killer T-cells); dendritic cells, NK cells and NKT cells are also encompassed in the invention. Bacterial cells, such as E. coli, may be employed to generate the polynucleotide that encodes the HER2-CAR, for example.

In one aspect, provided herein is a cell that has been genetically engineered to express one or more CARs. In certain embodiments, the genetically engineered cell is, e.g., a T lymphocyte (T-cell), a natural killer (NK) T-cell, or an NK cell. In certain other embodiments, the genetically engineered cell is a non-immune cell, e.g., a mesenchymal stem cell (MSC), a neuronal stem cell, a hematopoietic stem cell, an induced pluripotent stem cell (iPS cell), or an embryonic stem cell, for example. In specific embodiments, the cell also comprises an engineered CAR or any other genetic modification that may enhance its function. In a particular embodiment, the antigen binding domain of the CAR binds HER2, although in certain embodiments the antigen binding domain of a CAR recognizes a different target antigen.

The cells can be autologous cells, syngeneic cells, allogenic cells and even in some cases, xenogeneic cells.

In many situations one may wish to be able to kill the genetically engineered T-cells, where one wishes to terminate the treatment, the cells become neoplastic, in research where the absence of the cells after their presence is of interest, or other purpose. For this purpose one can provide for the expression of certain gene products in which one can kill the engineered cells under controlled conditions, such as inducible suicide genes. Such suicide genes are known in the art, e.g., the iCaspase9 system in which a modified form of caspase 9 is dimerizable with a small molecule, e.g., AP1903. See, e.g., Straathof et al., *Blood* 105:4247-4254 (2005).

It is further envisaged that the pharmaceutical composition of the disclosure comprises a host cell transformed or transfected with a vector defined herein. The host cell may be produced by introducing at least one of the above described vectors or at least one of the above described nucleic acid molecules into the host cell. The presence of the at least one vector or at least one nucleic acid molecule in the host may mediate the expression of a gene encoding the above described be specific single chain antibody constructs.

The described nucleic acid molecule or vector that is introduced in the host cell may either integrate into the genome of the host or it may be maintained extrachromosomally.

The cells encompassed by the disclosure may also comprise a proteinaceous compound capable of providing an activation signal for immune effector cells useful for cell proliferation or cell stimulation. In the light of the present disclosure, the "proteinaceous compounds" providing an activation signal for immune effector cells may be, e.g. a further activation signal for T-cells (e.g. a further costimulatory molecule: molecules of the B7-family, OX40 L, 4-1BBL), or a further cytokine: interleukin (e.g. IL-2, IL-7, or IL-15), or an NKG-2D engaging compound. The proteinaceous compound may also provide an activation signal for immune effector cell, which is a non-T-cell. Examples for immune effector cells which are non-T-cells comprise, inter alia, NK cells, or NKT-cells.

One embodiment relates to a process for the production of a composition of the disclosure, the process comprising culturing a host cell defined herein above under conditions allowing the expression of the construct, and the cell or a plurality of cells is provided to the individual.

The conditions for the culturing of cells harboring an expression construct that allows the expression of the CAR molecules are known in the art, as are procedures for the purification/recovery of the constructs when desired.

In one embodiment, the host cell is a genetically engineered T-cell (e.g., cytotoxic T lymphocyte) comprising a CAR and in particular embodiments the cell further comprises an engineered TCR. Naturally occurring T-cell receptors comprise two subunits, an α-subunit and a β-subunit, each of which is a unique protein produced by recombination event in each T-cell's genome. Libraries of TCRs may be screened for their selectivity to particular target antigens. An "engineered TCR" refers to a natural TCR, which has a high-avidity and reactivity toward target antigens that is selected, cloned, and/or subsequently introduced into a population of T-cells used for adoptive immunotherapy. In contrast to engineered TCRs, CARs are engineered to bind target antigens in an MHC independent manner.

VI. Polynucleotide Encoding CARs

The present disclosure also encompasses cells comprising a nucleic acid sequence encoding a CAR as defined herein and cells harboring the nucleic acid sequence. The nucleic acid molecule is a recombinant nucleic acid molecule, in particular aspects and may be synthetic. It may comprise DNA, RNA as well as PNA (peptide nucleic acid) and it may be a hybrid thereof.

It is evident to the person skilled in the art that one or more regulatory sequences may be added to the nucleic acid molecule comprised in the composition of the disclosure. For example, promoters, transcriptional enhancers and/or sequences that allow for induced expression of the polynucleotide of the disclosure may be employed. A suitable inducible system is for example tetracycline-regulated gene expression as described, e.g., by Gossen and Bujard (Proc. Natl. Acad. Sci. USA 89 (1992), 5547-5551) and Gossen et al. (Trends Biotech. 12 (1994), 58-62), or a dexamethasone-inducible gene expression system as described, e.g. by Crook (1989) EMBO J. 8, 513-519.

Furthermore, it is envisaged for further purposes that nucleic acid molecules may contain, for example, thioester bonds and/or nucleotide analogues. The modifications may be useful for the stabilization of the nucleic acid molecule against endo- and/or exonucleases in the cell. The nucleic acid molecules may be transcribed by an appropriate vector comprising a chimeric gene that allows for the transcription of said nucleic acid molecule in the cell. In this respect, it is also to be understood that such polynucleotides can be used for "gene targeting" or "gene therapeutic" approaches. In another embodiment the nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

The nucleic acid molecule(s) may be a recombinantly produced chimeric nucleic acid molecule comprising any of the aforementioned nucleic acid molecules either alone or in combination. In specific aspects, the nucleic acid molecule is part of a vector.

The present disclosure therefore also relates to a composition comprising a vector comprising the nucleic acid molecule described in the present disclosure.

Many suitable vectors are known to those skilled in molecular biology, the choice of which would depend on the function desired and include plasmids, cosmids, viruses, bacteriophages and other vectors used conventionally in genetic engineering. Methods that are well known to those skilled in the art can be used to construct various plasmids and vectors; see, for example, the techniques described in Sambrook et al. (1989) and Ausubel, Current Protocols in Molecular Biology, Green Publishing Associates and Wiley Interscience, N.Y. (1989), (1994). Alternatively, the polynucleotides and vectors of the disclosure can be reconstituted into liposomes for delivery to target cells. A cloning vector may be used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCAL-n-EK, pESP-1, pOP13CAT.

In specific embodiments, there is a vector that comprises a nucleic acid sequence that is a regulatory sequence operably linked to the nucleic acid sequence encoding a CAR construct defined herein. Such regulatory sequences (control elements) are known to the artisan and may include a promoter, a splice cassette, translation initiation codon, translation and insertion site for introducing an insert into the vector. In specific embodiments, the nucleic acid molecule is operatively linked to said expression control sequences allowing expression in eukaryotic or prokaryotic cells.

It is envisaged that a vector is an expression vector comprising the nucleic acid molecule encoding a CAR construct defined herein. In specific aspects, the vector is a viral vector, such as a lentiviral vector. Lentiviral vectors are commercially available, including from Clontech (Mountain View, Calif.) or GeneCopoeia (Rockville, Md.), for example.

The term "regulatory sequence" refers to DNA sequences that are necessary to effect the expression of coding sequences to which they are ligated. The nature of such control sequences differs depending upon the host organism. In prokaryotes, control sequences generally include promoters, ribosomal binding sites, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the recited vector is an expression vector, in certain embodiments. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the PL, lac, trp or tac promoter in *E. coli*, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements that are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pEF-Neo, pCDM8, pRc/CMV, pcDNA1, pcDNA3 (Invitrogen), pEF-DHFR and pEF-ADA, (Raum et al. Cancer Immunol Immunother (2001) 50(3), 141-150) or pSPORT1 (GIBCO BRL).

In some embodiments, the expression control sequences are eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the disclosure may follow.

Additional regulatory elements may include transcriptional as well as translational enhancers. Advantageously, the above-described vectors of the disclosure comprises a selectable and/or scorable marker. Selectable marker genes useful for the selection of transformed cells are well known to those skilled in the art and comprise, for example, antimetabolite resistance as the basis of selection for dhfr, which confers resistance to methotrexate (Reiss, Plant Physiol. (Life-Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* that confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green/red/mcherry fluorescent protein (Gerdes, FEBS Lett. 389 (1996), 44-47) or beta-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule can be used in a cell, alone, or as part of a vector to express the encoded polypeptide in cells. The nucleic acid molecules or vectors containing the DNA sequence(s) encoding any one of the CAR constructs described herein is introduced into the cells that in turn produce the polypeptide of interest. The recited nucleic acid molecules and vectors may be designed for direct introduction or for introduction via liposomes, or viral vectors (e.g., adenoviral, retroviral) into a cell. In certain embodiments, the cells are T-cells, CAR T-cells, NK cells, NKT-cells, MSCs, neuronal stem cells, or hematopoietic stem cells, for example.

In accordance with the above, the present disclosure relates to methods to derive vectors, particularly plasmids, cosmids, viruses and bacteriophages used conventionally in genetic engineering that comprise a nucleic acid molecule encoding the polypeptide sequence of a CAR defined herein. In certain cases, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the recited polynucleotides or vector into targeted cell populations. Methods that are well known to those skilled in the art can be used to construct recombinant vectors; see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the disclosure can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

VI. Kits of the Disclosure

Any of the compositions described herein may be comprised in a kit. In a non-limiting example, cells, lipid bilayers or reagents to generate bilayers, labels, antigens, vectors, substrates, and so forth may be comprised in a kit.

The component(s) of the kits may be packaged either in aqueous media or in lyophilized form, and they may be frozen. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow-molded plastic containers into which the desired vials are retained.

The components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Visualization of CAR T Synapse by Two Complementary Systems

To test whether CAR T cells can form a stable IS, both kappa-CAR and CD19-CAR were added to the glass-supported planar lipid bilayers carrying fluorescently labeled kappa and CD19 tumor antigen, respectively. The CAR constructs were described previously. Briefly, a retroviral vector containing the single-chain antibody against the CD19 molecule or kappa chain protein, the CD28 intracellular domain (hereinafter referred to as CD28-CAR) or CD28 intracellular domain linked with 4-1BB endodomain (hereinafter referred to as 4-1BB-CAR), and the zeta chain of TCR. Kappa-CAR and CD19-CAR share the same intracellular domains, as shown in FIG. 11. The distributions of CAR were imaged by 3-dimensional (3D) STED super-resolution microscopy (FIG. 1). Images of fixed CAR T cells on lipid bilayers revealed a central accumulation of kappa and CD19 under each CAR T cell, which is reminiscent of the central cluster of the T-cell receptor (TCR) and B-cell receptor (BCR) at the synapse. In addition to the structure of the synapse, the intracellular downstream signaling molecule-pZeta (a critical molecule for CAR signaling) and F-actin (an essential component for maintaining the synapse stability), as well as perforin (a marker for lytic granules) were also investigated. To visualize the distribution of phosphorylation of the zeta chain, an Ab against the phosphorylated zeta chain at tyrosine 83 (Y83) was used to stain pZeta at the IS. As expected, pZeta was co-localized with the kappa or CD19 antigen, a ligand on lipid bilayers, which can directly mirror the distribution of CAR on the T cells. Meanwhile, a strong accumulation of F-Actin and polarization of perforin were observed at the IS, indicating a functional CAR synapse formation on the glass-supported planar lipid bilayer.

There is a consideration that the glass-supported planar lipid bilayer system cannot fully mimic the complex surface of a tumor cell. To further demonstrate that the synapse formation observed on the glass-supported planar lipid bilayer can be recapitulated on CAR T cells with their real susceptible tumor cells, a high-throughput VCP image device was developed that allows one to visualize the IS between CAR T and its susceptible tumor cells in a vertical focal plane in a high-resolution manner. The kappa chain positive Daudi cell line was loaded into this VCP device first, followed by CAR T cells. Similarly, images of fixed CAR T cells showed an accumulation of both kappa and CD19 at the IS. Both F-actin and perforin were polarized at the CAR T IS (FIG. 1). Thus, a CAR T cell can form a functional IS, measured by structure, signaling, and function by imaging on two complementary systems.

Superior Quality of IS Formed by 4-1 BB-CAR T Cells

Figure 2A:
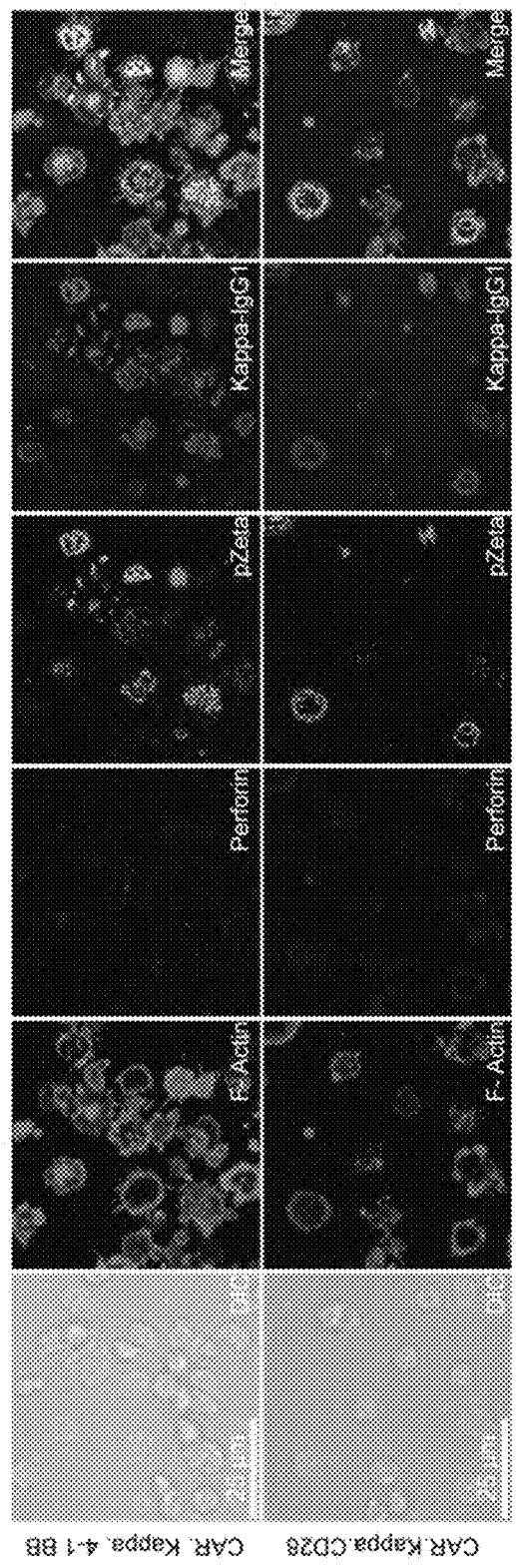
FIG. 2: Quantitative quality of IS formed by 4-1BB-CAR and CD28-CAR T cells (a) Confocal microscope of kappa-4-1BB-CAR T and kappa-CD28-CAR T cells on lipid bilayer carrying human kappa IgG1-Alexa Fluor 647 (red). Fixed and permeabilized CAR.T cells were stained for perforin (green), pZeta (cyan), and F-actin (magenta). Scale bars represent 25.0 (b) Quantification of IS on the lipid bilayer-T cell focal plane by measuring the mean intensity of F-actin, pZeta, and kappa cluster, as well as the percentage of perforin-positive cells on the lipid bilayers containing kappa IgG1. Error bars show±standard deviation (s. d.). Data represents three independent experiments.
Figure 2B:
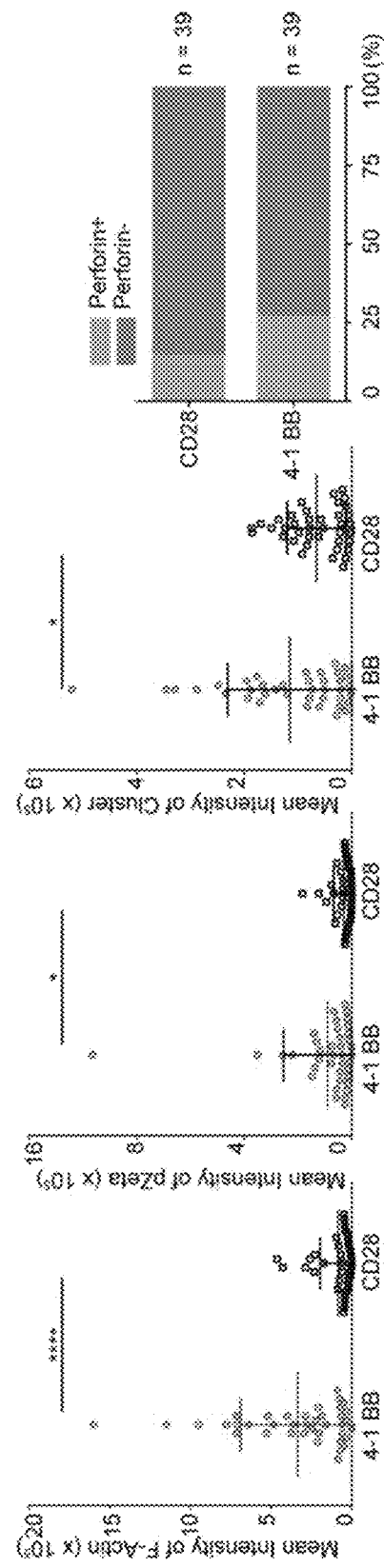
Figure 7A:
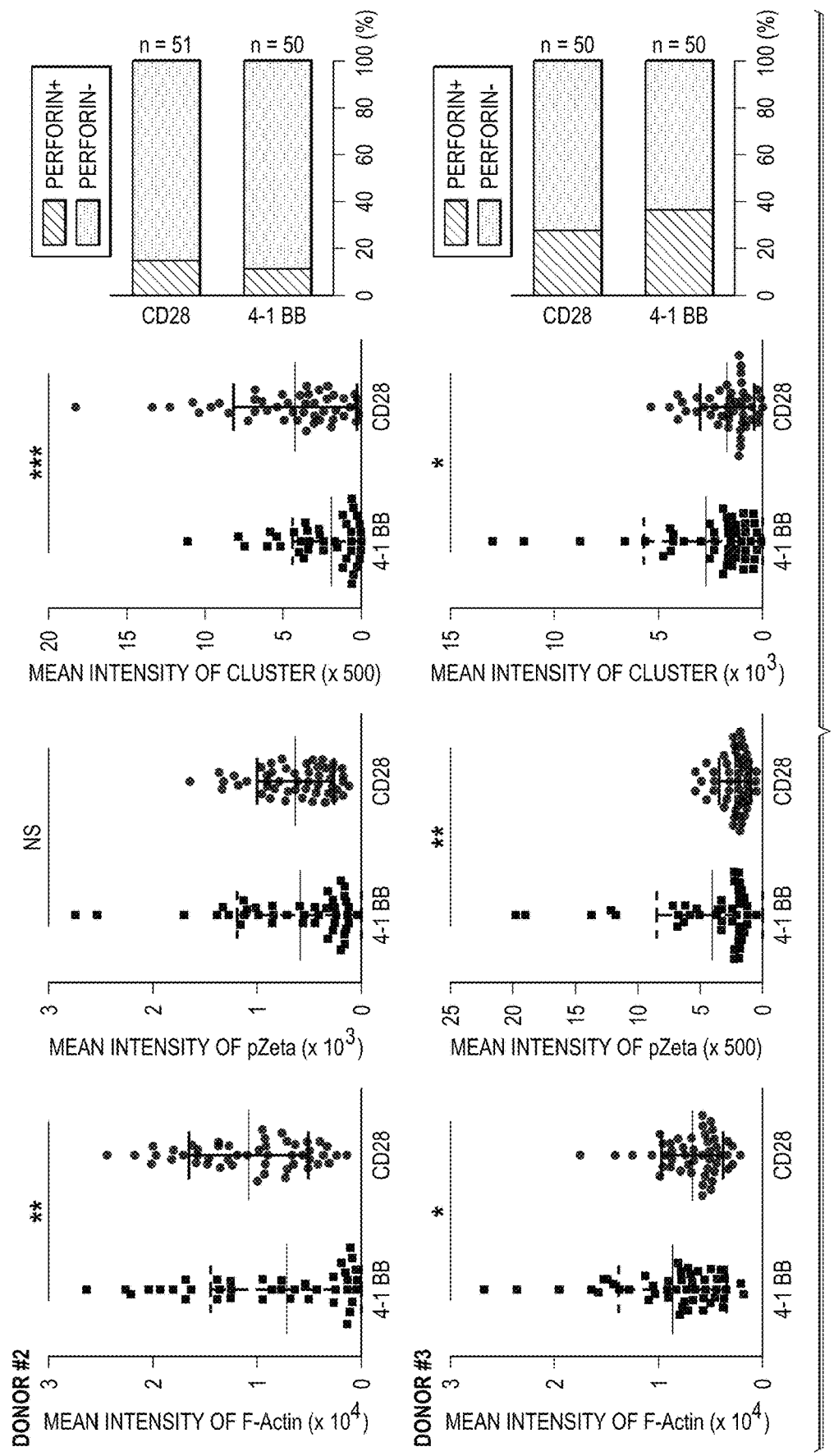
FIG. 7a,b: Quantification of IS quality. CAR T cells were added to the lipid bilayer containing Alexa Fluor 647 labeled kappa IgG1. Cells were stained with Abs against perforin, pZeta, and phalloidin. Quantification of the IS under the lipid bilayer by measuring the mean intensities of F-actin, pZeta, and kappa cluster, as well as the percentage of perforin-positive cells on lipid bilayer containing kappa IgG1. Error bars show±s.d.
Figure 7B:
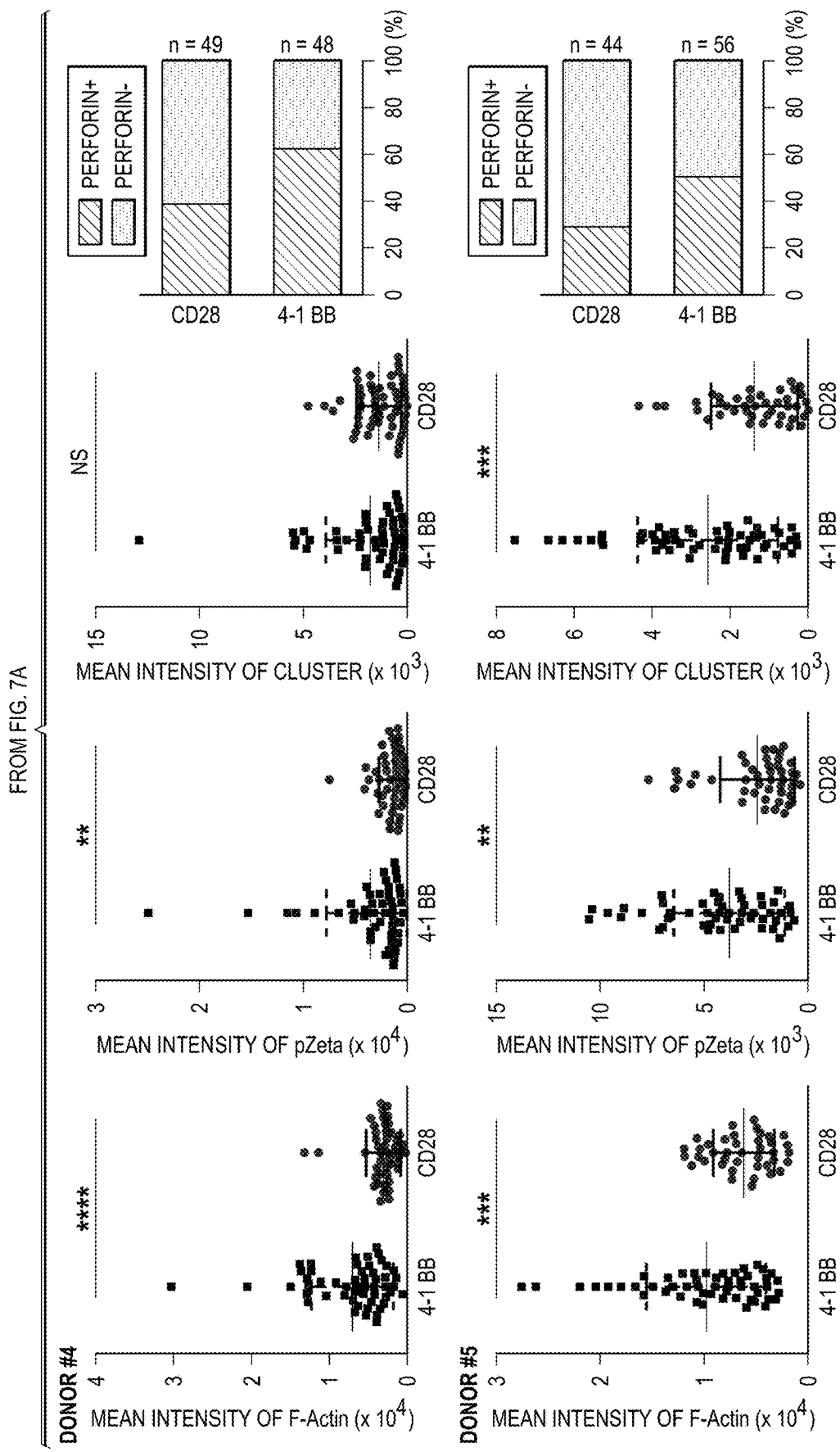
Figure 8A:
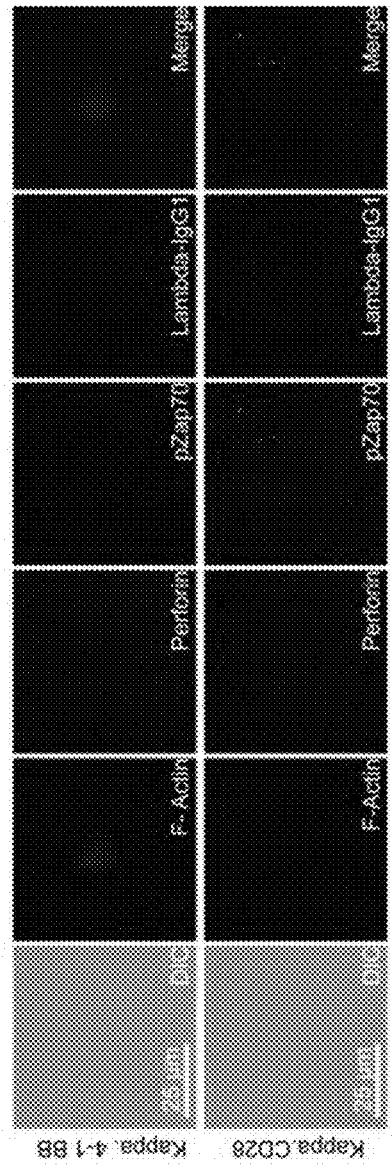
FIG. 8: Specific interactions between kappa-CAR T cells and the lipid bilayer carrying kappa antigen. Confocal images of 4-1BB- and CD28-CAR T cells. CAR T cells on the lipid bilayer carrying Alexa Fluor 647-labeled Kappa IgG1 (b) or Lambda IgG1 (a, control). Fixed CAR T cells were stained for perforin (green), pZap70 (yellow or cyan), LCK (green) and F-actin (magenta). Scale bars represent 25.0 μm. (c) Quantification of the mean intensities of F-Actin, pZAP70, cluster of kappa, and the percentage of perforin. Error bars show±s.d.

Different intracellular domains of CAR can mediate different anti-tumor activities. Given the CAR synapse formation described above in two different CAR T cells, it was considered that the quality of the IS (quantitation of its structure, signaling, and function) built by 4-1BB-CAR is different from that of the CD28-CAR T cell. To test this hypothesis, the inventors quantitatively compared the structure, signaling, and function of the IS. Strikingly, stronger F-actin, pZeta, and central cluster of tumor antigen staining were observed in 4-1BB-CAR T cells, compared to CD28-CAR T cells derived from the same donor (FIG. 2). Interestingly, both 4-1BB-CAR T cells and CD28-CAR T cells can accumulate the kappa antigen on the lipid bilayers. Although the distributions of the kappa clusters in these two CARs are similar, the mean fluorescence intensity of the kappa cluster in the 4-1BB-CAR T cells is significantly higher than that of the CD28-CAR T cells (FIG. 2b), suggesting a better anti-tumor activity mediated by 4-1 BB co-stimulatory domains. Quantitative results for kappa-CAR IS from other four donors were summarized (FIG. 7a,b). Significantly increased pZeta from 4-1BB-CAR T cells was observed from four out of five donors. As a control, CAR T cells were added to the bilayers carrying fluorescently labeled lambda IgG1 (FIG. 8a). No cells interacted with the lipid bilayer containing lambda IgG1 (FIG. 8a). No clustering in response to lambda IgG1 was observed for either 4-1BB- or CD28-CAR T cells, which suggests specific interactions and synapse formations by CAR T cells on lipid bilayers carrying their susceptible tumor antigens.

Figure 8B:
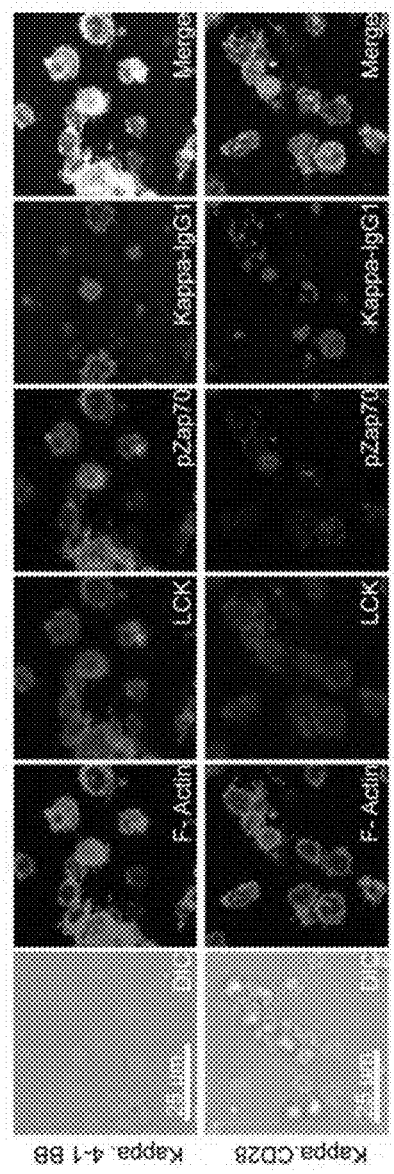
Figure 8C:
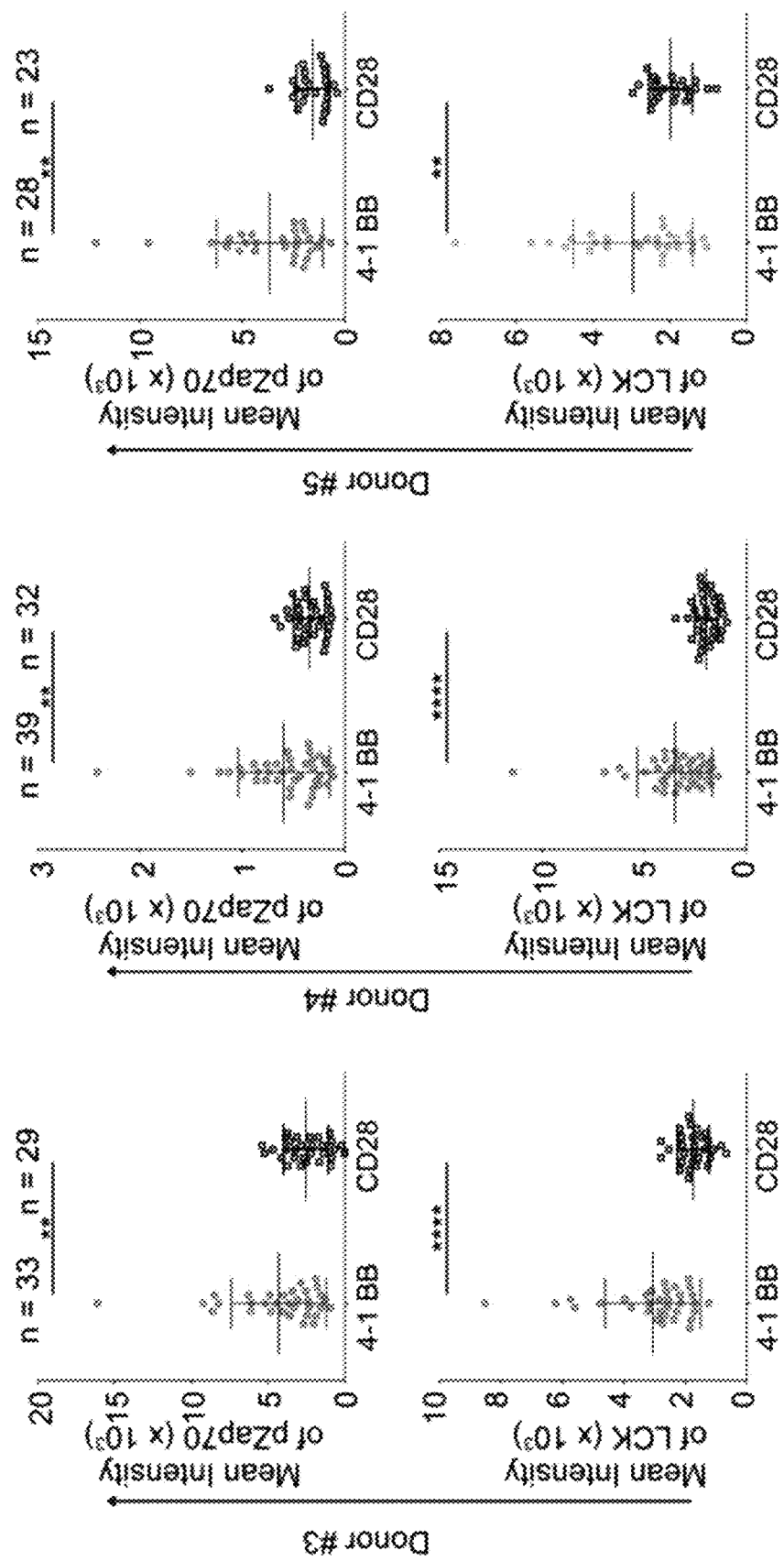
Figure 9B:
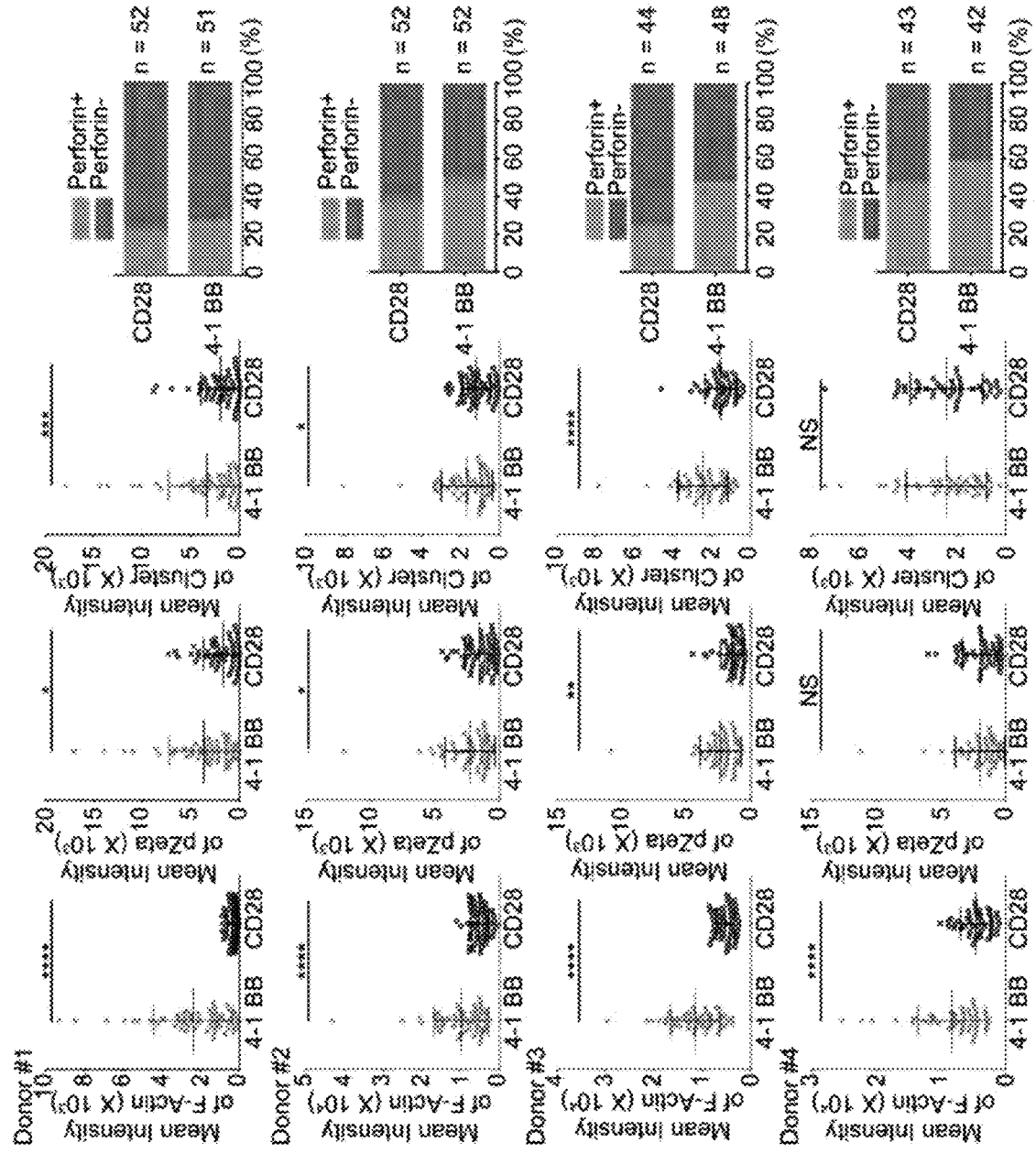
FIG. 9: Superior IS quality in CD19 specific 4-1BB.CAR T cells. (a) Confocal microscope of CD19-CAR T cells with 4-1BB or CD28 activated on lipid bilayer carrying CD19-Alexa Fluor 568 (red). Fixed and permeabilized CD19-CAR T cells were stained for perforin, and pZeta and then incubated with phalloidin, Alexa Fluor 532 (magenta), Alexa Fluor 647-(green), and Alexa Fluor 488-(cyan) conjugated secondary Abs respectively. Scale bars represent 25.0 μm. (b) Quantification of IS under the lipid bilayer by measuring the mean intensities of F-actin, pZeta, and CD19 cluster, as well as the percentage of perforin-positive cells on lipid bilayer containing CD19. Error bars show±s.d.

In addition to pZeta (a proximal CAR signaling molecule), more distal CAR signaling pathways, pZAP70 (zeta chain associated protein 70) and Lck (lymphocyte specific protein tyrosine kinase), at the CAR T synapse were also investigated. As expected, the kappa IgG1 protein on the lipid bilayer triggered both pZAP-70 and Lck (FIGS. 8b, c). These two signaling molecules are involved in the long-term proliferation and differentiation of the activated T lymphocytes. Similar results were also obtained from CD19-CAR (FIG. 9), which confirms a broad, superior effect of 4-1BB co-stimulatory domains. Together, the data demonstrated a superior synapse quality elicited by 4-1BB-CAR T cells, compared to CD28-CAR T cells.

Example 2

Figure 3A:
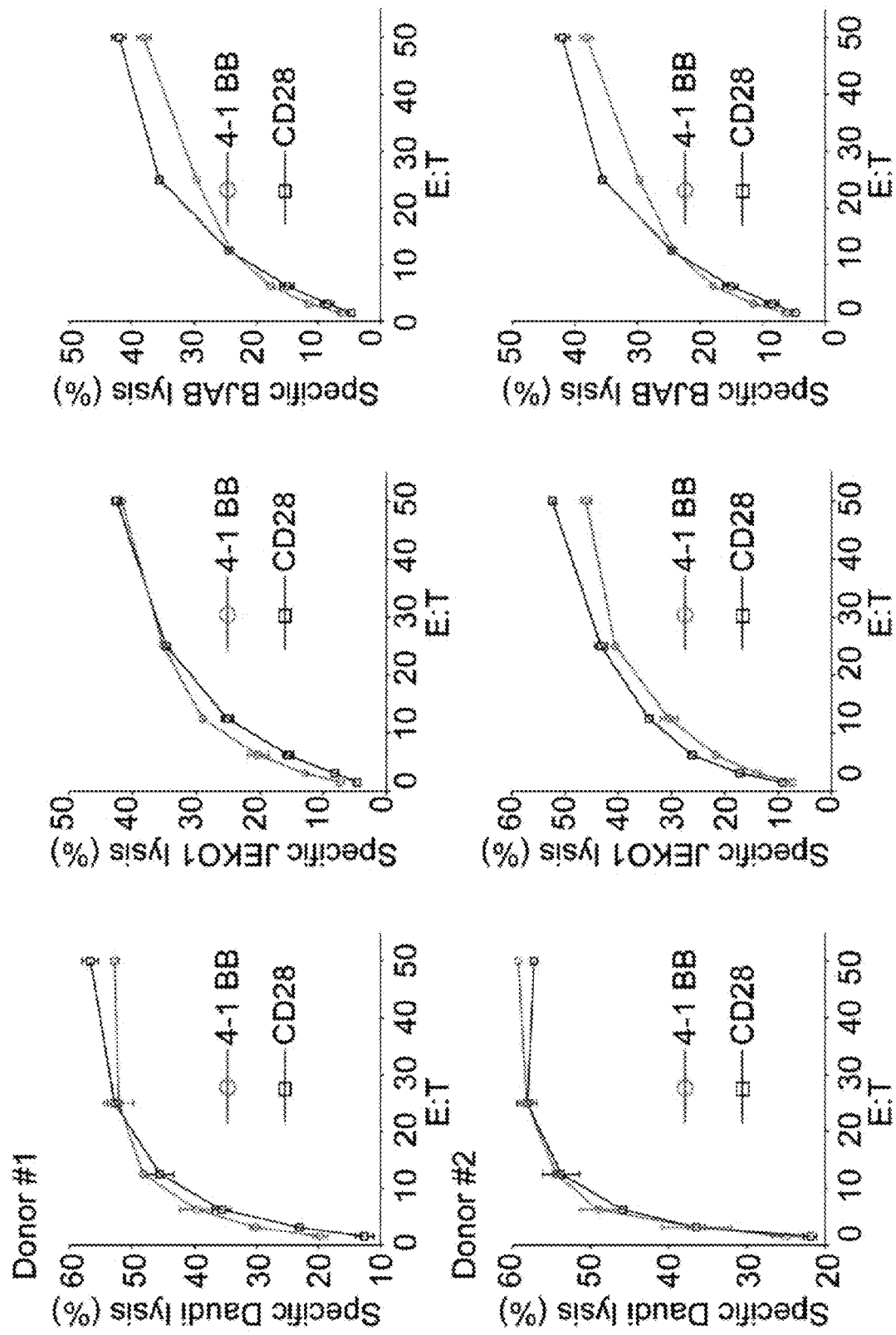
FIG. 3: Standard $Cr^{51}$ release assay and intracellular cytokine assay cannot distinguish the difference between 4-1BB-CAR and CD28-CAR. The cytotoxicity of kappa-CAR T (a) and CD19-CAR (b) cells from two healthy donors (Donor #1 and #2) was measured using 4-h $^{51}Cr$-release assay. Three kappa positive B-cell lymphoma cell lines (Daudi, JEKO1, and BJAB) were used as kappa-CAR T cell's target cells. Error bars show±s. d. The two CD19 positive B-cell lymphoma cell lines (Daudi and Raji) were used as the target cells. Error bars show±s. d. PBMCs from five individuals were transduced with 4-1BB construct (red dots) or CD28 construct (black dots) retrovirus. The secretion of TNF-α and IFN-γ by the kappa-CAR (c) and CD19 (d). CAR was measured by the flow cytometry after stimulation with target cells for 6 hours with the Golgistop and Brefildin A treatment. The percentage of TNF-α or IFN-γ positive cells was measured.
Figure 3B:
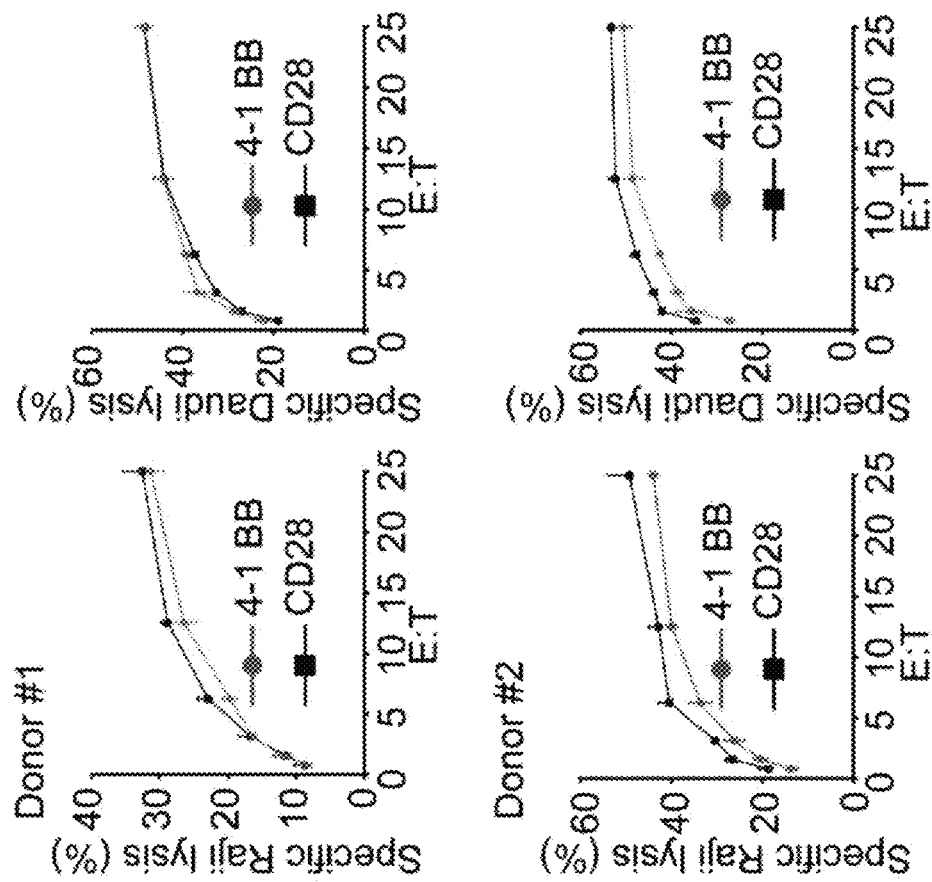

Standard $CR^{51}$ Release Assay and Cytokine Secretion Cannot Distinguish the Difference Between 4-1BB-CAR and CD28-CAR T Cells Optimal function of T cells depends on the quality of the synapse. Given the superior quality of the synapse built by 4-1BB-CAR T cells, in one embodiment 4-1BB-CAR T cells can elicit better killing activity against their susceptible tumor cells. To test this consideration, the standard 4-hour $Cr^{51}$ release assay was used to measure the cytotoxicity of CAR T cells, as well as intracellular cytokine secretion. Comparing the cytotoxicity of 4-1BB-CAR T cells and CD28-CAR T cells, both 4-1BB-CAR T and CD28-CAR T cells efficiently killed their susceptible tumor cells (FIG. 3a). However, both 4-1BB CAR T and CD28-CAR T cells displayed the similar activity against three different kappa chain positive tumor cell lines: Daudi, JEKO1, and BJAB cells (FIG. 3a). Similar results were obtained in CD19-CAR T cells against two CD19 positive tumor cell lines—Raji and Daudi cells (FIG. 3b). Meanwhile, the production of TNF-α and IFN-γ by both kappa-CAR and CD19-CAR between CD28-CAR and 4-1BB-CAR from five individuals is comparable (FIGS. 3c and 3d). Therefore, in specific embodiments the 4-hour standard $Cr^{51}$ release and secretion of conventional cytokine assays cannot distinguish the difference between CD28.CAR T cells and 4-1BB CAR T cells.

Example 3

Enhanced Anti-Tumor Activity in 4-1BB-CAR T Cells

Figure 4B:
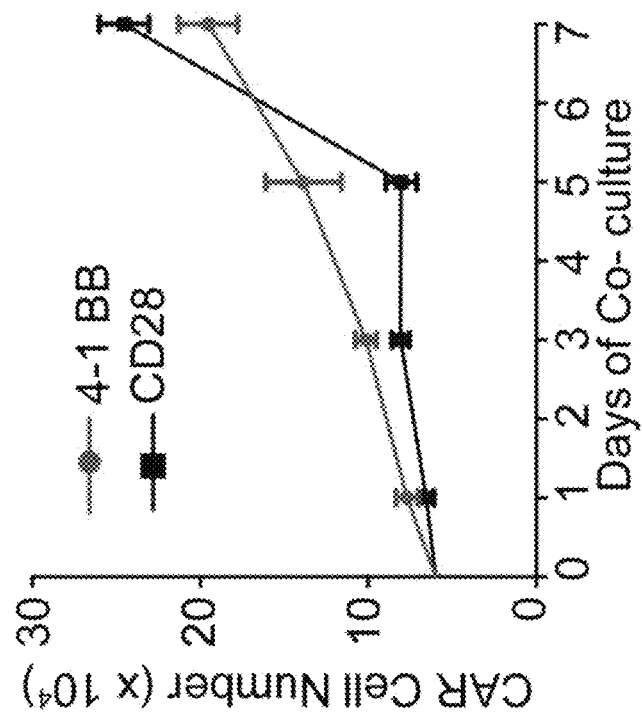
FIG. 4: Superior anti-tumor activity from 4-1BB CAR T cells was measured by long-term killing assay. (a) Diagram of experimental design for serial killing assay. (b and c) Anti-tumor effects of kappa-CAR (b) and CD19-CAR (c) were measured by the decrease in tumor cells (left) and increase in effector cells (right). Kappa-positive Daudi cell expressing fluorescent protein mCherry was used as a target cell.
Figure 4B:
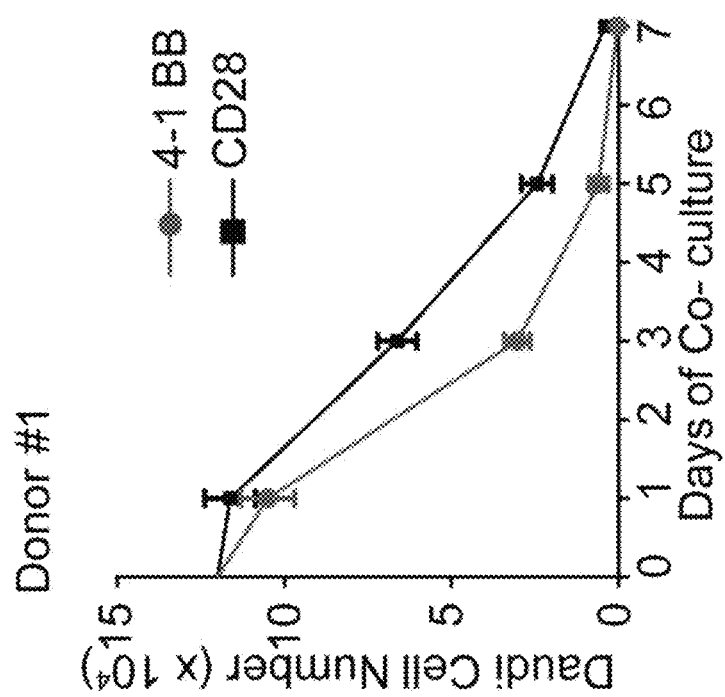
Figure 4C:
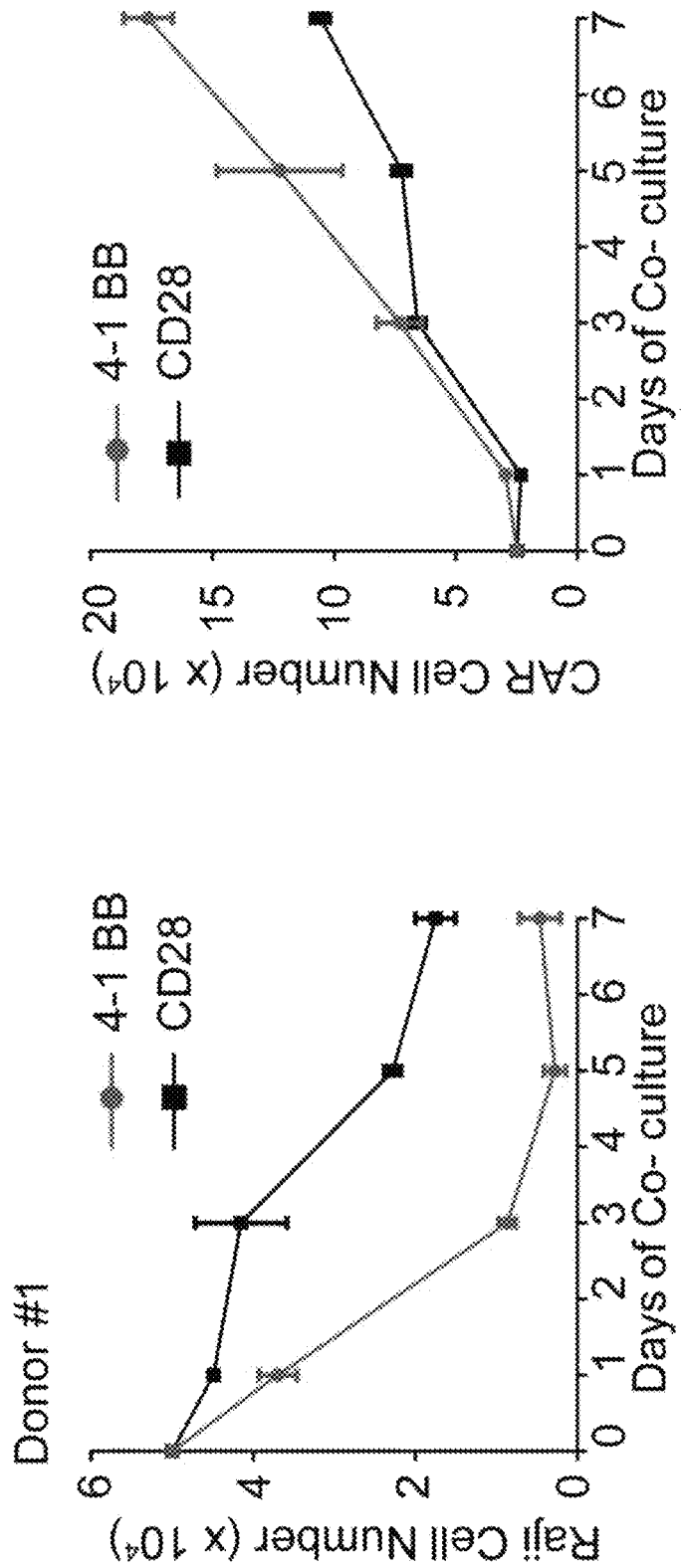
Figure 10A:
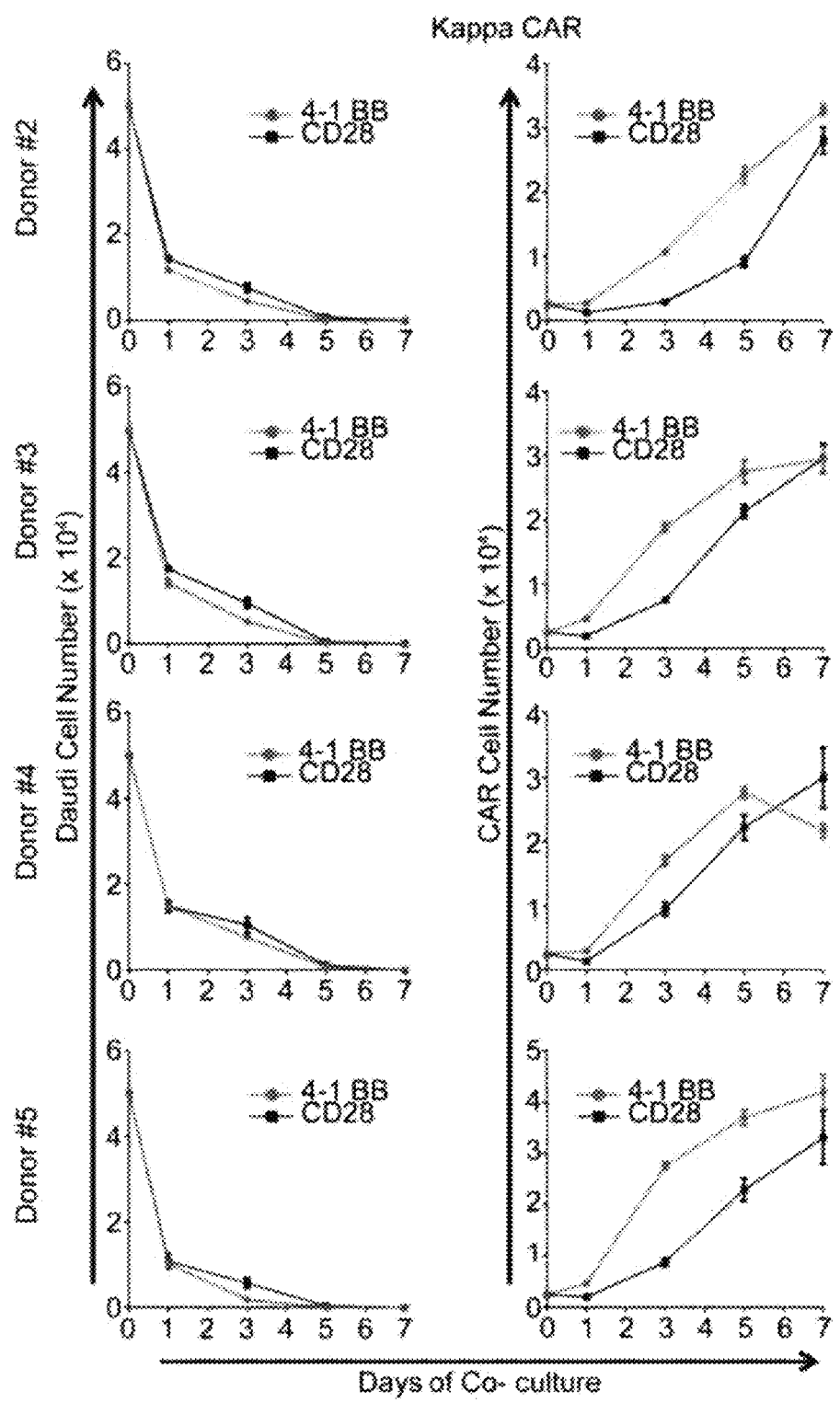
FIG. 10: 4-1 BB.CAR T cells have enhanced antitumor activity and proliferation.
Figure 10B:
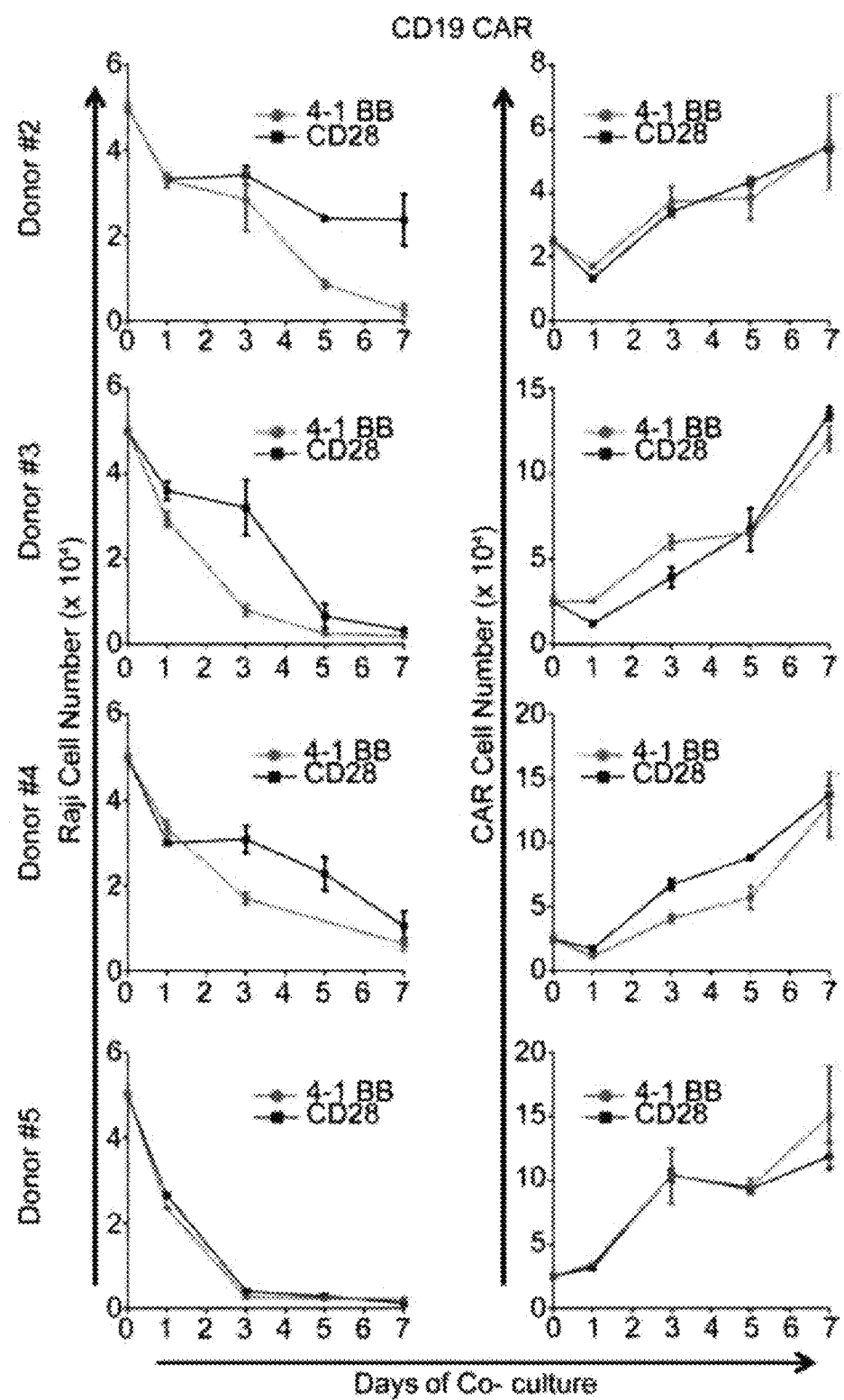

Previous studies have shown that the anti-tumor activity of CAR T cells depends on CAR T cell activation, persistence, and proliferation. To further examine whether 4-1BB-CAR T cells show better anti-tumor activity, CAR T cells were co-cultured with their susceptible target Daudi cell expressing red fluorescent protein mCherry (Daudi-mCherry) or Raji cell expressing green fluorescent protein (GFP) (Raji-GFP), which can measure not only the eradication of tumor cells but also the proliferation of CAR T cells. During a one-week co-culture period, both residual tumor cell numbers (hereinafter referred to as 'tumor-killing activity') were quantified and expanded CAR T cell numbers (hereinafter referred to as 'effector cell proliferation') by flow cytometry (FIG. 4a). As expected, both 4-1BB-CAR T cells and CD28-CAR T cells efficiently eliminated kappa-chain positive Daudi cells (FIG. 4b) or Raji cells (FIG. 4c). Interestingly, 4-1BB-CAR T cells eradicated their susceptible tumor cells more rapidly. Meanwhile, the proliferation capability of CAR T cells is a critical parameter for measuring the effectiveness of CAR T cells. Longer persistence of CAR T cells in patients can enhance the effectiveness of CAR T cells. The proliferation capability of the CAR T cell was further measured by quantifying the CAR T cell numbers during co-culturing with their susceptible tumor cells. The proliferation capability of 4-1BB CAR T cells derived from different kappa-CAR and CD19-CAR specificities increased significantly, as compared to that of CD28 co-stimulatory domain CAR T cells (FIG. 4). Similar results from four other four donors for K.CAR T cells (FIG. 10a) and four other donors for CD19-CAR T cells (FIG. 10b) were obtained. Quantitative data from five individuals further showed the significantly enhanced anti-tumor activity in 4-1BB CAR T cells, compared to CD28-CAR T cells (FIG. 11). In summary, the results showed that the 4-1 BB co-stimulatory domain enhanced the anti-tumor activity.

Example 4

Quality of IS Correlates Positively with Effectiveness of CAR T Cells In Vitro

Figure 5A:
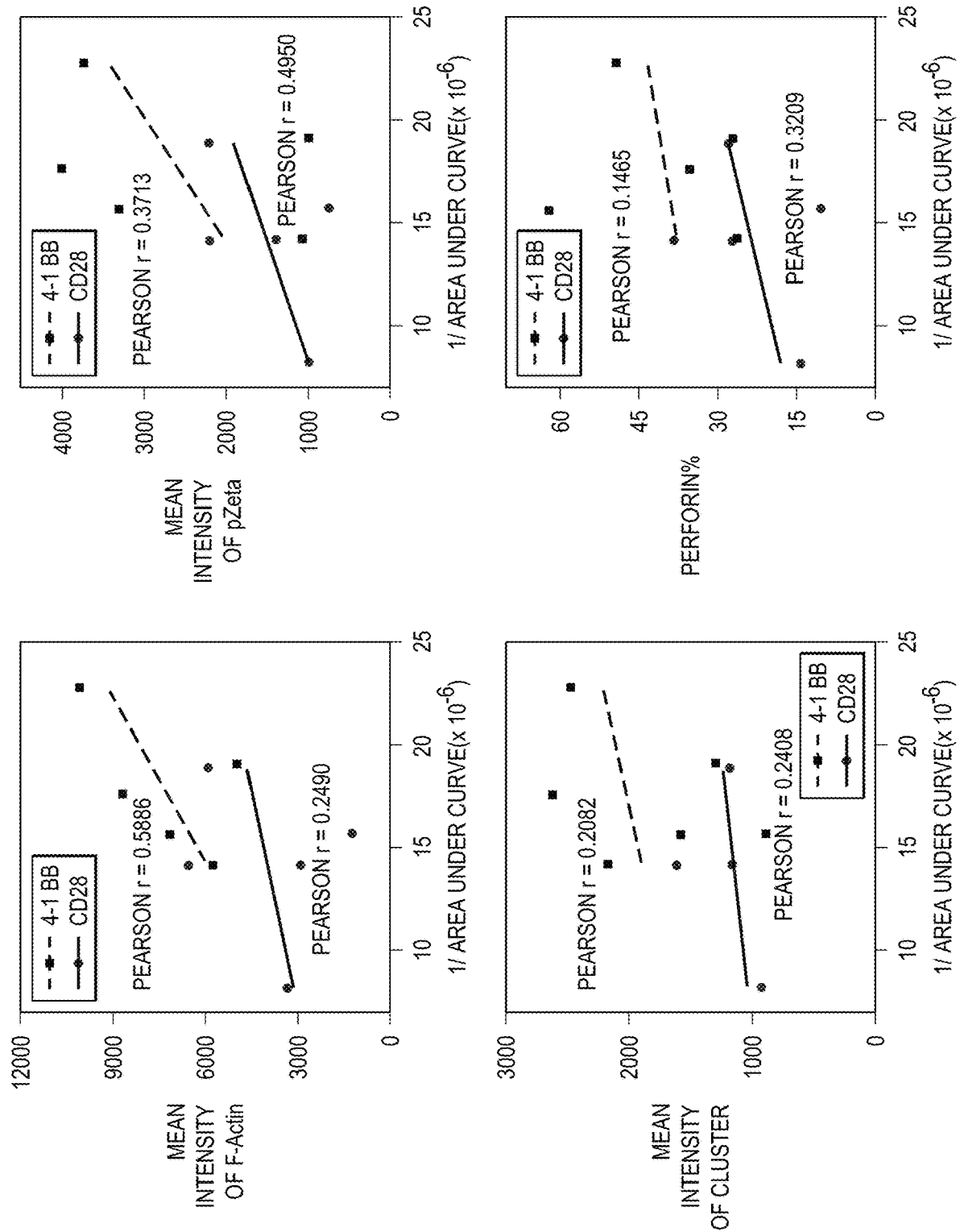
FIG. 5: Positive Correlation between anti-tumor effects and IS quality. (a) Correlation analysis between the quality of the synapse and the killing efficiency (the reciprocal of area under the curve of tumor cell numbers). (b) Correlation analysis between the quality of the synapse and the proliferation efficiency (the area under the curve of T cell numbers). The quality of the synapse was measured by the intensities of F-Actin, pZeta, and cluster of tumor antigen, as well as the percentage of perforin. The Pearson r-value was calculated. Each dot represents one donor.
Figure 5B:
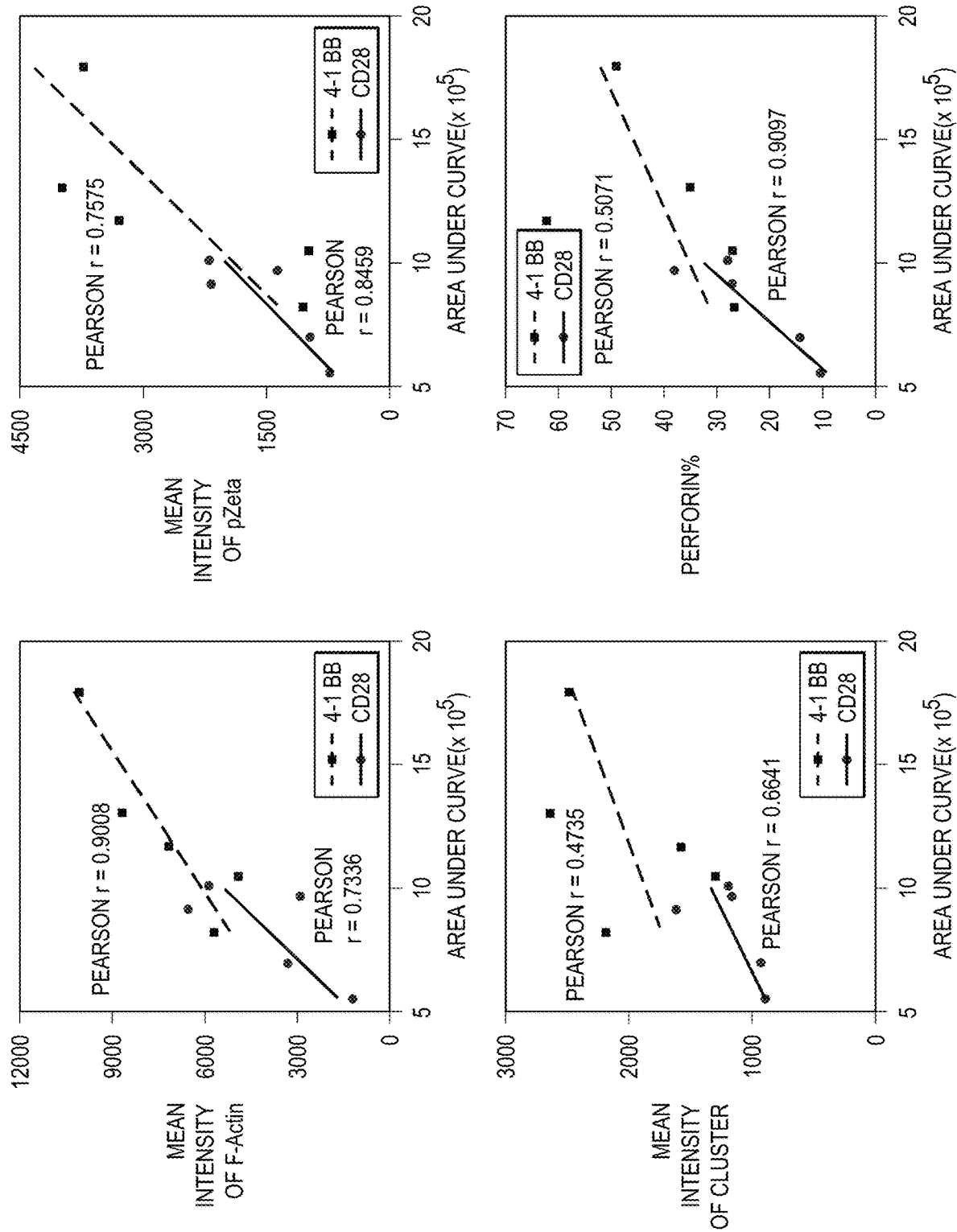

Given the higher quality of the IS (quantitation of structure and signaling molecules within the IS) observed in 4-1BB CAR T cells, in at least certain embodiments it was considered that the quality of IS correlates positively with the effectiveness of CAR T cells. If so, one can predict the effectiveness of Kappa-CAR-T and CD19-CAR-T cells by evaluating the quality of the IS. To test this consideration, an accumulation of pZeta and F-actin, cluster of tumor antigen, and polarization of lytic granule was used to measure the quality of the IS, while the anti-tumor activity of CAR T cells from the same donor was measured. To quantify the effectiveness of the CAR T cells, the reciprocal of the area under the curve of tumor cell numbers (hereinafter referred to as 'killing efficiency') and the area under the curve of T cell numbers (hereinafter referred to as 'proliferation efficiency') in long-term killing assay was used. Quantitative data from five individuals further showed the significantly higher quality of the IS in 4-1BB-CAR T cells, compared to CD28-CAR T cells (FIG. 12). 4-1BB CAR T cells from five donors showed a positive correlation between the qualities of the IS and killing efficiency (FIG. 5a), as well as proliferation efficiency (FIG. 5b). Thus, the quality of the IS correlates positively with the effectiveness of CAR T cells. Hence, in specific embodiments of the disclosure the quality of the IS can predict the effectiveness of CAR T cells.

Significance of Certain Embodiments

Cancer immunotherapy has been investigated for more than 124 years, since surgeon William Coley began injecting patients with cancer with bacteria (*Streptococcus pyogenes*) in 1891. Recent progress in CAR T cell-mediated immunotherapy delivers promise for curing various cancers. Currently, the mechanisms proposed for explaining the effectiveness of the CAR T cell focuses mainly on the capabilities of cytokine secretion, cytotoxicity, proliferation, and homing to the tumor site. However, the exact molecular mechanisms at the level of the single cell remain unclear. Specifically, the synapse between the CAR T and its susceptible target cells has not been studied, although the IS has been studied for more than three decades in the field of basic immunology. For the first time, provided herein is detailed information about the CAR synapse. Both CD19-CAR and Kappa-CAR T cells formed a stable IS on the glass-supported planar lipid bilayer carrying the corresponding tumor antigens such as CD19 and kappa molecules, as well as their susceptible target cells in a newly-developed, novel VCP imaging device. Importantly, the quality of the synapse can be used to predict directly the effectiveness of the CAR T cell in vitro, which provides a novel strategy for clinicians to assess the CAR T cell in a cost-effective manner. Meanwhile, the VCP system can achieve high-resolution images with conventional image approaches such as confocal microscopy, without the need for super-resolution microscopy. Therefore, the inventors not only demonstrated a unique feature of the CAR synapse but also provided the immunotherapy field with a new approach to predict the effectiveness of CAR T cells in vitro.

The commonality between the CAR synapse and the TCR-mediated synapse is intriguing. Both CAR and TCR accumulate at the center of the synapse. CD19-CAR and kappa-CAR accumulated at the center of the synapse upon stimulation of the CAR. After accumulation of surface artificial receptor expressing on CAR T cells, these centralized CAR can trigger the downstream signaling cascades. Strong accumulation of key signaling molecules such as pZeta was observed, which is reminiscent of the accumulation of proximal TCR signaling molecules, a hallmark feature of T cell activation. Accumulation of F-actin at IS plays an important role in T cell synapse formation and also was observed at the CAR synapse in this study. One of the critical outcomes of accumulation of F-actin at the synapse is the polarization of lytic granules towards target cells. Similarly, the polarization of lytic granules has been observed in the activated CAR T cells in two complementary systems. Both CAR and TCR induce a F-actin ring at the synapse, but F-actin was not completely depleted at the center of the synapse, which is consistent with the previous observations in human NK cells. Thus, CAR T cells use a mechanism for cytotoxicity similar to that of cytotoxic lymphocytes.

Provided herein is a study of the quality of the IS compared between CD28- and 4-1BB-CAR, a common second generation of CAR. The quality of the IS was evaluated by quantifying the mean intensity of the tumor antigens on lipid bilayers (structure of CAR synapse), the mean intensity of key signaling molecules (signaling cascades at CAR synapse), accumulation of F-actin, and polarization of lytic granules (function of CAR synapse). The quality of the synapse, measured by structure, signaling, and function, built by the 4-1BB CAR is superior to that of the CD28-CAR, which could explain the better tumor control and clinical outcomes from 4-1BB-CAR immunotherapy.

In vivo persistence and expansion of adoptively transferred CAR T cells are crucial to obtaining sustained clinical response. Precisely predicting and evaluating the quality and effectiveness of CAR T cells represents the major effect in the field of immunotherapy. 4-hour $Cr^{51}$ release assay is a standard approach for measuring cytotoxicity of lymphocytes, which has been widely used to evaluate the cytotoxicity of lymphocytes. This assay, however, could not effectively distinguish the difference in effectiveness between CD28- and 4-1BB-CAR T cells. In specific embodiments, the long-term killing assay serves as a better way to evaluate the effectiveness of CAR T cells. Significant differences between CD28- and 4-1BB-CAR in both controlling the numbers of tumor cells and T cell expansion have been observed, which positively correlates with the quality of the synapse. In summary, provided herein is not only a novel tool to predict the effectiveness of CAR T cell by quantifying the quality the IS, but also the first description of CAR T synapse.

Example 5

Examples of Materials and Methods

Cell Lines

The following cell lines were used: Daudi, JEKO1, BJAB and Raji (CD19+ Burkitt's lymphoma cell lines). All the cell lines were purchased from American Type Culture Collection (Manassas, Va., USA). Cell lines were maintained in RPMI-1640 (Gibco, San Francisco, Calif., USA) supplied with 10% fetal bovine serum (Hyclone, Waltham, Mass., USA) and 2 mM L-glutamine (Gibco).

Plasmid Construction and Retrovirus Production

Figure 6:
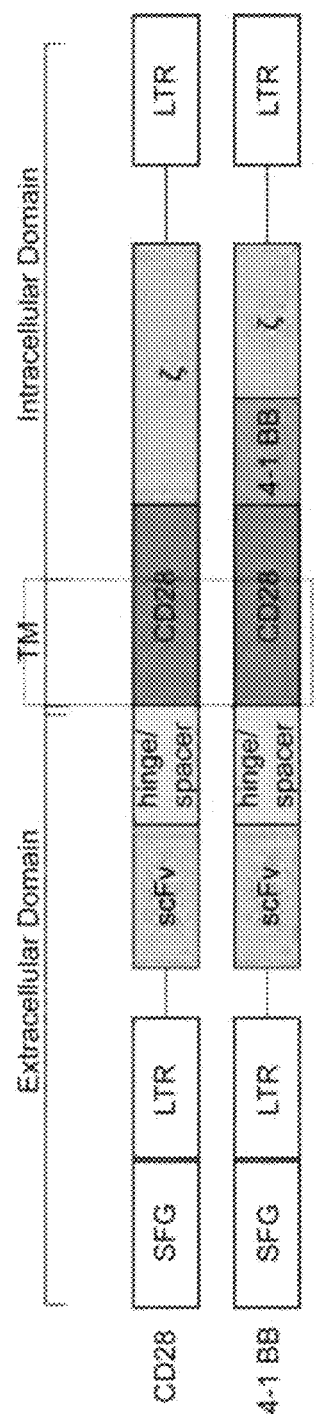
FIG. 6: Schematic representation of recombinant retroviral vectors encoding CAR. Both kappa- and CD19-CAR constructs contain CD28 transmembrane domain and intracellular domain of zeta.

The CAR constructs were described previously. Briefly, both the kappa and CD19 scFv sequences were cloned in a SFG retroviral backbone in frame with the hinge of the human IgG1 and the ζ-chain of the human TCR/CD3 complex (FIG. 6). All of the constructs contain a transmembrane domain of CD28 to ensure equal expression of the CAR constructs. Retroviral supernatants were produced by transfecting 293T cells with a combination of chimeric antigen containing plasmids, RDF plasmid encoding the RD114 envelope, and PegPam3 plasmid encoding the MoMLV gag-pol as previously described.

Generation of CAR-Modified T Cells

Peripheral blood mononuclear cells (PBMCs) were obtained from healthy donors according to the approved protocols. To transduce the PBMCs, cells were activated with 1 μg/ml anti-CD3 (clone, OKT3, Ortho Biotech, Bridgewater, N.J., USA) and 1 μg/ml anti-CD28 with 100 U/ml recombinant human IL-2 (Proleukin; Chiron, Emeryville, Calif., USA) in 10% FBS RPMI-1640 media. Activated T cells were transduced with retroviral supernatants on day 3 in plates coated with recombinant fibronectin fragment (FN CH-296; Retronectin; Takara Shuzo, Otsu, Japan). After transduction, T cells were expanded using IL-2 and then used for assays.

$Cr^{51}$ Release Assay

To evaluate the cytotoxic activity of CAR+ T lymphocytes, standard 4-h $^{51}Cr$ release assay was used. Briefly, target cells were labeled with $^{51}Cr$ at 37° C. for 1 hour and then re-suspended at 1×10$^5$/ml in RPMI medium with 10% FBS. 1×10$^4$ target cells were incubated with serial-diluted CAR+ T cells at 37° C. for 4 hours. After centrifugation, the supernatants were collected and the released $^{51}Cr$ was measured with a gamma counter (Wallac, Turku, Finland). The cytotoxicity (%) was calculated as follows: (sample–spontaneous release)/(maximum release–spontaneous release)×100.

Intracellular Cytokine Staining

The CAR T cells were suspended with pre-warmed R10 medium containing Brefeldin A (20 μl/ml, Sigma-Aldrich) and Golgi Stop (1.4 μl/ml, BD). The target cells were added into the wells to stimulate the CAR T cells for 6 hours in the incubator. After stimulation, the cells were stained with the viability dye followed by surface staining with CD3 (Clone OKT3, Biolegend, San Diego, Calif., USA), CD4 (Clone OKT4, Biolegend, San Diego, Calif., USA) and CD8 (Clone RPA-T8, Biolegend, San Diego, Calif., USA) antibodies. After washing with PBS, the cells were permeabilized with BD Cytofix/Ctyoperm buffer (BD) for 20 minutes at room temperature, and then were washed with 1× BD/Wash buffer twice. The cells were stained with the intracellular antibodies, including TNF-α (Clone MAb11, Biolegend, San Diego, Calif., USA) and IFN-γ (Clone B27, Biolegend, San Diego, Calif., USA).

Long-Term Killing Assay

To evaluate the anti-tumor activity of CAR T cells in a long term, a long-term killing assay was used. Briefly, CAR T cells were co-cultured with the kappa light-chain positive Daudi cell expressing fluorescent protein mCherry or CD19+ Raji-GFP at the effector and target (E:T) with a ratio of 1:2. After the indicated days of mixture, cells were analyzed by flow cytometry.

Glass-Supported Planar Lipid Bilayer

Planar lipid bilayers were prepared by fusing small liposome droplets with clean glass coverslips as described. Briefly, the liposome was trapped in a μ-Slide VI$^{0.4}$ chamber (Ibidi, Germany) Lipid bilayers were first blocked with 5% Casein for 30 min and then incubated with 6.3 nM Streptavidin (Life Technologies) for 20 min. After being washed extensively with imaging buffer (HEPES-buffered saline), bilayers were incubated with biotinylated antibodies conjugated with Alexa Fluor dyes at room temperature for 30 min. After getting a second wash with imaging buffer, bilayers were blocked with 2.5 μM D-biotin to saturate the streptavidin-binding sites. Cells were activated on the lipids for 60 min.

Confocal Imaging on the Planar Lipid Bilayer

CAR+ T cells were stimulated on lipid bilayers containing either fluorescently labeled kappa or CD19 proteins. Cells were stained by fluorescently conjugated antibodies against perforin (deltaG9, Thermo), pZeta (phosphor-Y83, Abcam), LCK (3A5, Santa Cruz) and pZAP70 (Tyr 319, Cell Signaling), as described previously. F-actin was stained by Alexa Fluor 532-conjugated phalloidin (Life Technology). A Leica TCS SP8 microscope (Leica, Germany) was used to obtain confocal image data.

Conjugation Experiment on the Device

The VCP device is composed of two polydimethylsiloxane (PDMS) layer-micropit and microtrap arrays. Prior to seeding the cell, the VCP device was pre-coated with 2% bovine serum albumin (BSA) in PBS. Then, R10 medium was used to replace the BSA solution in the device. 10 μl of the effector cell suspension with a concentration range of 10$^6$-10$^7$ cells/ml was added into the inlet. 20 μl R10 medium was withdrawn by a 1 ml syringe to generate flow. After 30 seconds of seeding, the remainder of the cell suspension was washed with medium. The microfluidic device was centrifuged at 2000 rpm for 10 min to spin down the cells into a micropit array. Target cells were stained with eFlour®450 (Ebioscience, 65-0842-85) and were added into the inlet. The parameters for seeding the second cell suspension were the same as those for the first cell suspension.

For fixed-cell imaging, the device was incubated for 1 hour at 37° C. to form a stable immunological synapse. The cell-cell conjugates were fixed by 4% formaldehyde solution in PBS for 15 minutes and then washed with PBS for 5 minutes. Permeabilization buffer containing 5% of normal donkey serum (NDS) and 0.5% Triton X-100 in PBS was flowed into the device for 1 hour. The permeabilization buffer was washed with PBS for 5 minutes. Then, primary antibodies in buffer containing 3% NDS and 0.5% Triton X-100 in PBS was pumped into the device. The device was incubated in 4° C. overnight. The antibody buffer was washed with PBS for 5 minutes. Cells were stained by fluorescently labeled secondary antibodies for 1 hour at room temperature. The antibody buffer was washed with PBS for 5 minutes, and, finally, a drop of ProLong Gold antifade reagent mounting medium (Life Technologies) was added into the device.

Statistical Analysis

Unpaired or paired two-tailed t-tests were performed using the Prism software (GraphPad Software, Inc., La Jolla, Calif., USA). The correlation between the quality of IS and the anti-tumor activity was analyzed by a linear regression correlation analysis (GraphPad).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

Moreover, the scope of the present application is not intended to be limited to the particular embodiments of the process, machine, manufacture, composition of matter, means, methods and steps described in the specification.

What is claimed is:

1. A method of determining the effectiveness of an immune cell comprising a chimeric antigen receptor (CAR), comprising the steps of:
   (a) providing a planar lipid bilayer comprising a plurality of labeled tumor antigens; and
   exposing the bilayer comprising the labeled tumor antigens to the immune cells comprising one or more CARs that target the antigen, thereby producing complexes of CARs bound to the antigen; or
   (b) providing tumor antigen-positive cells expressing labeled antigen; and
   exposing the tumor antigen-positive cells to the immune cells comprising one or more CARs that target the antigen, thereby producing complexes of CARs bound to the antigen; and
   (c) measuring the quality of an immunological synapse between CARs and the antigen by performing one or more of the following:
      (1) assaying for the distribution of labeled complexes in the lipid bilayer;
      (2) assaying for the intensity of labeled complexes in the lipid bilayer;
      (3) assaying for a phosphorylated form of the zeta chain of the T-cell receptor of the CAR or another signaling molecule involved in T cell activation;
      (4) assaying for accumulation of F-actin at the complexes;
      (5) assaying for polarization of perforin at the complexes;
      (6) assaying for accumulation of zeta chain associated protein 70 (pZAP70) at the complexes; and
      (7) assaying for accumulation of lymphocyte specific protein tyrosine kinase (Lck) at the complexes;
   wherein the quality of the immunological synapse measured in (1) to (7) predicts the effectiveness of the immune cells comprising one or more CARs that target the antigen.

2. The method of claim 1, wherein in (b) the tumor antigen-positive cells expressing labeled antigen are fixed.

3. The method of claim 1, wherein in (b) the tumor antigen-positive cells expressing labeled antigen are live.

4. The method of claim 1, wherein the assaying for the phosphorylated form of the zeta chain of the T-cell receptor of the CAR comprises assaying for the intensity and/or localization of a signal from the phosphorylated form of the zeta chain.

5. The method of claim 4, wherein the assaying for the intensity and/or localization of the signal comprises exposing the complex to a labeled antibody to the phosphorylated form of the zeta chain.

6. The method of claim 1, wherein the assaying for the accumulation of F-actin at the complexes comprises assaying for the intensity and/or localization of a signal from F-actin.

7. The method of claim 6, wherein the assaying for the intensity and/or localization of the signal from F-actin comprises exposing the complex to a labeled antibody to F-actin.

8. The method of claim 1, wherein the assaying for the polarization of perforin at the complexes comprises assaying for the intensity and/or localization of a signal from perforin.

9. The method of claim 8, wherein the assaying for the intensity and/or localization of the signal from perforin comprises exposing the complex to a labeled antibody to perforin.

10. The method of claim 1, wherein the assaying for the accumulation of pZAP70 at the complexes comprises assaying for the intensity and/or localization of a signal from pZAP70.

11. The method of claim 10, wherein the assaying for the intensity and/or localization of the signal from pZAP70 comprises exposing the complexes to a labeled antibody to pZAP70.

12. The method of claim 1, wherein the assaying for the accumulation of Lck at the complexes comprises assaying for the intensity and/or localization of a signal from Lck.

13. The method of claim 12, wherein the assaying for the intensity and/or localization of the signal from Lck comprises exposing the complexes to a labeled antibody to Lck.

14. The method of claim 1, further comprising delivering a therapeutically effective amount of the immune cells expressing the CAR to an individual in need thereof.

15. The method of claim 14, wherein the individual has a cancer, is suspected of having a cancer, or is at risk for having a cancer.

16. The method of claim 1, wherein performing one or more of (1) to (7) comprises using microscopy.

17. The method of claim 16, wherein the microscopy comprises confocal microscopy, epifluorescence microscopy, structured illumination microscopy (SIM), photoactivated localization microscopy (PALM), stochastical optical reconstruction microscopy (STORM), or stimulated emission depletion microscopy (STED).

18. The method of claim 1, wherein in (b) the tumor antigen-positive cells expressing labeled antigen are provided on a vertical cell pairing (VCP) system or device.

* * * * *

UNITED STATES PATENT AND TRADEMARK OFFICE
CERTIFICATE OF CORRECTION

PATENT NO. : 10,732,170 B2
APPLICATION NO. : 15/749445
DATED : August 4, 2020
INVENTOR(S) : Dongfang Liu Page 1 of 1

It is certified that error appears in the above-identified patent and that said Letters Patent is hereby corrected as shown below:

On the Title Page

(73) Assignee: is listed as:
MISSUM BIOTECHOLOGY, LLC

Should be listed as:
MISUM BIOTECHNOLOGY, LLC

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*